United States Patent
Hironaka et al.

(10) Patent No.: US 10,478,786 B2
(45) Date of Patent: Nov. 19, 2019

(54) GAS SEPARATION MEMBRANE, GAS SEPARATION MODULE, GAS SEPARATION APPARATUS, AND GAS SEPARATION METHOD

(71) Applicant: FUJIFILM Corporation, Tokyo (JP)

(72) Inventors: Koji Hironaka, Kanagawa (JP); Keisuke Kodama, Kanagawa (JP); Satoshi Sano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 223 days.

(21) Appl. No.: 15/679,160

(22) Filed: Aug. 17, 2017

(65) Prior Publication Data
US 2018/0021740 A1  Jan. 25, 2018

Related U.S. Application Data

(63) Continuation of application No. PCT/JP2016/053141, filed on Feb. 3, 2016.

(30) Foreign Application Priority Data

Feb. 27, 2015  (JP) .................................. 2015-039093

(51) Int. Cl.
*B01D 71/64* (2006.01)
*B01D 61/36* (2006.01)
(Continued)

(52) U.S. Cl.
CPC ........... *B01D 71/64* (2013.01); *B01D 61/364* (2013.01); *B01D 71/80* (2013.01); *C08G 73/128* (2013.01);
(Continued)

(58) Field of Classification Search
CPC ...... B01D 53/22; B01D 53/228; B01D 69/12; B01D 71/62; B01D 71/64; B01D 71/70;
(Continued)

(56) References Cited

U.S. PATENT DOCUMENTS 5,591,250 A * 1/1997 Stern .................... B01D 53/228
95/51
8,241,501 B2  8/2012 Liu et al.
(Continued)

FOREIGN PATENT DOCUMENTS

JP  2007297605  11/2007
JP  2011523589  8/2011
(Continued)

OTHER PUBLICATIONS

English language machine translation for JP 2014-176795. Retrieved from http://translationportal.epo.org on May 7, 2019. (Year: 2019).*
(Continued)

*Primary Examiner* — Jason M Greene
(74) *Attorney, Agent, or Firm* — JCIPRNET

(57) ABSTRACT

A gas separation membrane has a gas separation layer containing a poly(benzoxazole-imide) compound in which the poly(benzoxazole-imide) compound having structural units represented by General formulae (I) and (II), or structural units represented by General formulae (I), (II) and (III) satisfies a specific molar quantity condition.

General formula (I)

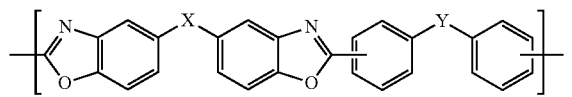

General formula (II)

(Continued)

-continued

General formula (III)

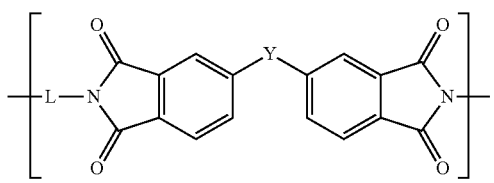

In the formulae, X and Y each represent a single bond or a specific divalent linking group; L represents a specific divalent linking group including a phenylene group; and R represents a specific group. A gas separation module and a gas separation method use the gas separation membrane. A gas separation apparatus includes the gas separation module.

27 Claims, 2 Drawing Sheets

(51) Int. Cl.
| | |
|---|---|
| B01D 71/80 | (2006.01) |
| C08G 73/12 | (2006.01) |
| C08G 77/455 | (2006.01) |
| C10L 3/10 | (2006.01) |
| C01B 32/55 | (2017.01) |
| B01D 53/14 | (2006.01) |
| C07C 9/04 | (2006.01) |

(52) U.S. Cl.
CPC ............ *C08G 77/455* (2013.01); *C10L 3/104* (2013.01); *B01D 53/1475* (2013.01); *C01B 32/55* (2017.08); *C07C 9/04* (2013.01)

(58) Field of Classification Search
CPC .............. B01D 71/80; B01D 2257/504; C08G 73/1085; C08G 73/22; C08G 77/455; C10L 3/104
See application file for complete search history.

(56) References Cited

U.S. PATENT DOCUMENTS

| | | | | |
|---|---|---|---|---|
| 2009/0282982 | A1* | 11/2009 | Jung | B01D 71/64 96/10 |
| 2010/0133186 | A1 | 6/2010 | Liu et al. | |
| 2010/0133190 | A1* | 6/2010 | Liu | B01D 53/228 210/650 |
| 2010/0137124 | A1 | 6/2010 | Liu et al. | |
| 2010/0242723 | A1 | 9/2010 | Liu et al. | |
| 2011/0072973 | A1 | 3/2011 | Liu et al. | |
| 2011/0077312 | A1 | 3/2011 | Liu et al. | |
| 2012/0085233 | A1 | 4/2012 | Liu et al. | |
| 2014/0033918 | A1* | 2/2014 | Zheng | B01D 53/228 95/51 |
| 2014/0047976 | A1 | 2/2014 | Yeong et al. | |
| 2015/0258505 | A1 | 9/2015 | Hironaka et al. | |

FOREIGN PATENT DOCUMENTS

| | | | | |
|---|---|---|---|---|
| JP | 2012521870 | | 9/2012 | |
| JP | 2012521871 | | 9/2012 | |
| JP | 2013505822 | | 2/2013 | |
| JP | 2014108391 | | 6/2014 | |
| JP | 2014-176975 | * | 9/2014 | ............ B01D 53/22 |

OTHER PUBLICATIONS

"Written Opinion of the International Searching Authority (Form PCT/ISA/237)" of PCT/JP2016/053141, dated May 17, 2016, with English translation thereof, pp. 1-11.
"International Search Report (Form PCT/ISA/210) of PCT/JP2016/053141", dated May 17, 2016, with English translation thereof, pp. 1-5.
"Office Action of Japan Counterpart Application," with machine English translation thereof, dated Jan. 30, 2018, p. 1-p. 8.

* cited by examiner

GAS SEPARATION MEMBRANE, GAS SEPARATION MODULE, GAS SEPARATION APPARATUS, AND GAS SEPARATION METHOD

CROSS-REFERENCE TO RELATED APPLICATIONS

This application is a Continuation of PCT International Application No. PCT/JP2016/053141 filed on Feb. 3, 2016, which claims priority under 35 U.S.C § 119(a) to Japanese Patent Application No. 2015-039093 filed on Feb. 27, 2015. Each of the above application(s) is hereby expressly incorporated by reference, in its entirety, into the present application.

BACKGROUND OF THE INVENTION

1. Field of the Invention

The present invention relates to a gas separation membrane, a gas separation module, a gas separation apparatus, and a gas separation method.

2. Description of the Related Art

Materials formed of polymer compounds each have gas permeability specific to the constituent materials. On the basis of this property, it is possible to cause selective permeation and separation of a desired gas component by using a membrane formed of a particular polymer compound. Regarding industrial applications of such a gas separation membrane, in relation to the issues of global warming, separation and recovery of carbon dioxide from large-scale sources of carbon dioxide emission have been examined in thermal power plants, cement plants, blast furnaces in steel mills, and the like. Furthermore, this membrane separation technique has been attracting attention as means capable of solving environmental problems with relatively low energy. In addition, natural gas and biogas (gas generated by fermentation or anaerobic digestion of excrement of organisms, organic fertilizers, biodegradable substances, sewage, garbage, and energy crops) are mixed gas containing mainly methane and carbon dioxide, and a membrane separation method has been examined as means for removing impurities such as carbon dioxide in such mixed gas (JP2007-297605A).

In purification of natural gas using the membrane separation method, good gas permeability and separation selectivity are desired in order to separate gas more efficiently. Various membrane materials have been examined in order to realize good gas permeability and separation selectivity. As part of these examinations, gas separation membranes using a polyimide compound or a polybenzoxazole compound have been examined (for example, U.S. Pat. No. 8,241,501B and JP2014-108391A).

SUMMARY OF THE INVENTION

In order to realize a practical gas separation membrane, it is necessary to reliably obtain sufficient gas permeability and gas separation selectivity by forming a gas separation layer as a thin layer. An example of the method therefor is a method that includes forming a polymer compound such as a polyimide compound into an asymmetric membrane by a phase separation process, so that a portion that contributes to separation is formed as a thin layer referred to as a dense layer or a skin layer. In this asymmetric membrane, a portion other than the dense layer is allowed to function as a support layer which provides the membrane with mechanical strength.

Besides the asymmetric membrane, a form of a composite membrane is also known in which a material which provides a gas separation function and a material which provides mechanical strength are different from each other. This composite membrane has a structure in which a gas separation layer that is a thin layer formed of a polymer compound is formed on a gas-permeable support which provides mechanical strength.

In actual plants, membranes are plasticized by, for example, the influence of high-pressure conditions and impurities (for example, benzene, toluene, and xylene) that are present in natural gas, resulting in a problem of a decrease in separation selectivity. Accordingly, resistance to impurities such as toluene is also an important factor for practical application of gas separation membranes.

In addition, since gas separation membranes are usually used under high-pressure conditions, the membranes are required to have sufficient mechanical strength such that membrane defects are not generated, even under high-pressure conditions. Furthermore, gas separation membranes are usually used in the form of a package which is referred to as a module or an element and is filled with a gas separation membrane. Such a package is filled with a gas separation membrane at a high density in order to ensure a large membrane surface area. For example, a flat-membrane-form gas separation membrane fills a package in a state of being folded in a spiral manner and is used as a gas separation module. Accordingly, gas separation membranes are required to have flexibility (folding endurance) in addition to mechanical strength.

An object of the present invention is to provide a gas separation membrane which realizes both gas permeability and gas separation selectivity at a high level, which is unlikely to be plasticized, even in the presence of impurities such as toluene, which exhibits good gas separation performance, even under high-temperature, high-pressure, and high-humidity conditions, which exhibits good folding endurance, and which is capable of being produced at a high yield. Another object of the present invention is to provide a gas separation module, a gas separation apparatus, and a gas separation method using the above gas separation membrane.

In view of the problems described above, the inventors of the present invention conducted extensive research. As a result, the inventors found that the above objects can be achieved by forming a thin membrane by using a polyimide compound having particular structural units, subsequently subjecting the membrane to heat treatment to convert the polyimide compound to a poly(benzoxazole-imide) compound, and using the resulting membrane as a gas separation layer. Further research that was conducted on the basis of this finding led to the completion of the present invention.

The above objects have been achieved by means described below.

A first aspect of the present invention provides a gas separation membrane having a gas separation layer containing a poly(benzoxazole-imide) compound. The poly(benzoxazole-imide) compound satisfies a condition (A) or (B).

(A) The poly(benzoxazole-imide) compound has a structural unit represented by General formula (I) and a structural unit represented by General formula (II), and in the poly(benzoxazole-imide) compound, a molar quantity m of the structural unit represented by General formula (I) and a molar quantity n of the structural unit represented by General formula (II) satisfy Mathematical expression 1.

(B) The poly(benzoxazole-imide) compound has the structural unit represented by General formula (I), the structural unit represented by General formula (II), and a structural unit represented by General formula (III), and in the poly(benzoxazole-imide) compound, the molar quantity m of the structural unit represented by General formula (I), the molar quantity n of the structural unit represented by General formula (II), and a molar quantity q of the structural unit represented by General formula (III) satisfy Mathematical expression 2.

$$0.25 \le m/n \le 9.00 (0<n) \quad \text{Mathematical expression 1:}$$

$$0.25 \le m/(n+q) \le 9.00 (0<n, 0<q) \quad \text{Mathematical expression 2:}$$

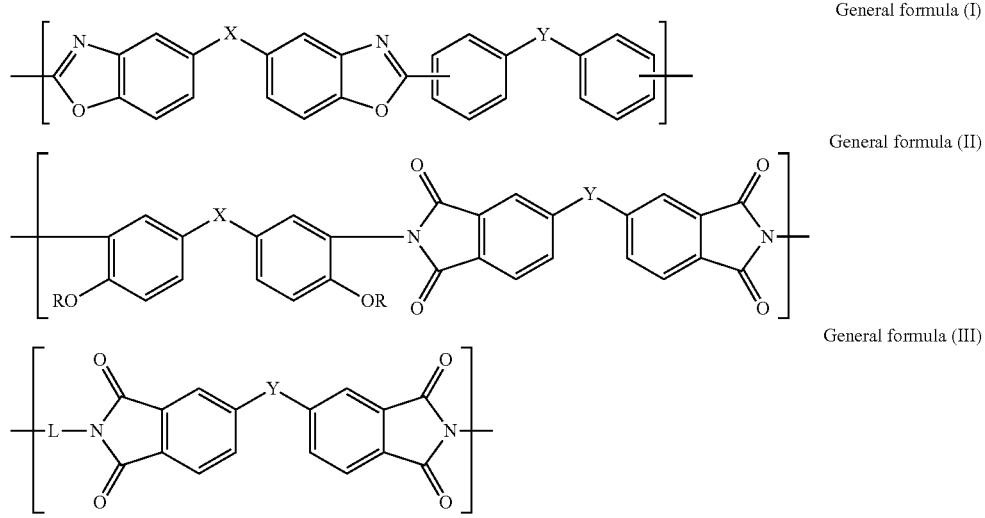

General formula (I)

General formula (II)

General formula (III)

In the formulae, X and Y each represent a single bond, a divalent linking group selected from Group (IV), or a divalent linking group formed by combining one or two or more linking groups selected from Group (IV); L represents a divalent linking group including a phenylene group provided that the phenylene group does not have an —OR group as a substituent; and R represents a hydrogen atom, $COR^1$, or $Si(R^2)_3$ where $R^1$ and $R^2$ each represent an alkyl group.

Group (IV)

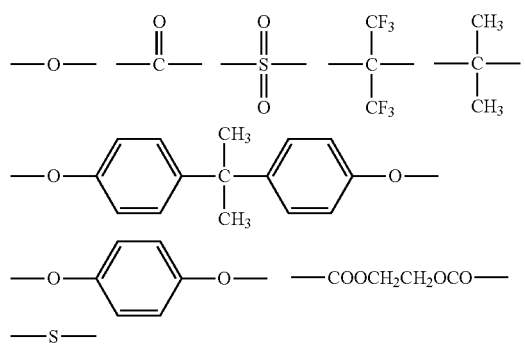

The poly(benzoxazole-imide) compound preferably satisfies the condition (B), and L is a divalent linking group selected from Group (V).

Group (V)

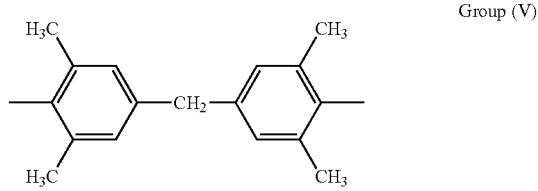

-continued

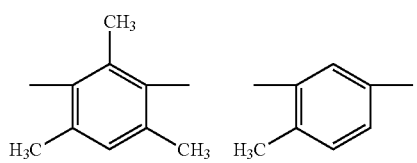

L is preferably a divalent linking group represented by the following formula.

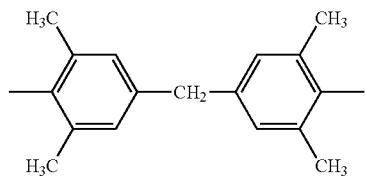

Y is preferably a single bond or a divalent linking group selected from Group (IV-1).

(Group (IV-1))

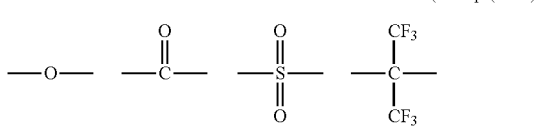

Y is preferably a divalent linking group selected from Group (IV-2).

Group (IV-2)

Y is preferably a divalent linking group represented by the following formula.

X is preferably a single bond or a divalent linking group represented by the following formula.

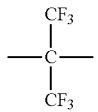

The gas separation layer preferably further contains a polymer other than the poly(benzoxazole-imide) compound.

The gas separation layer is preferably a layer formed by heat-treating a layer containing a polyimide compound having a structural unit represented by General formula (VI) and a structural unit represented by General formula (VII):

where X, Y, and L respectively have the same definition as X, Y, and L in General formulae (II) and (III); and $R^Z$ represents a hydrogen atom, $COR^1$, or $Si(R^2)_3$. where $R^1$ and $R^2$ each represent an alkyl group $R^Z$ is preferably $COR^1$ or $Si(R^2)_3$.

$R^Z$ is preferably $COR^1$ where $R^1$ represents an alkyl group.

$R^Z$ is preferably $COCH_3$.

$R^Z$ is preferably $Si(R^2)_3$ where $R^2$ represents an alkyl group.

A temperature of the heat-treating is preferably 300° C. to 600° C.

The gas separation membrane is preferably an asymmetric membrane.

The gas separation membrane preferably further has a siloxane compound layer disposed on the gas separation layer. A Si ratio of the siloxane compound layer after immersion in chloroform to the siloxane compound layer before immersion in chlorofoemn, the Si ratio being calculated by Mathematical expression (I), is 0.6 to 1.0.

Si ratio=(Si–KαX-ray intensity after immersion in chloroform)/(Si–KαX-ray intensity before immersion in chloroform)   Mathematical expression (I)

The siloxane compound layer preferably contains an organopolysiloxane compound having a structure in which siloxane compounds are linked to each other through a linking group selected from the group consisting of *—O—M-O—*, *—S-M-S—*, *—$NR^aC$(=O)—*, *—$NR^bC$(=O)$NR^b$—*, *—O—$CH_2$—O—*, *—S—$CH_2CH_2$—*, *—OC(=O)O—*, *—CH(OH)$CH_2$OCO—*, *—CH(OH)$CH_2$O—*, *—CH(OH)$CH_2$S—*, *—CH(OH)$CH_2NR^c$—*, *—CH($CH_2$OH)$CH_2$OCO—*, *—CH($CH_2$OH)$CH_2$O—*, *—CH($CH_2$OH)$CH_2$S—*, *—CH($CH_2$OH)$CH_2NR^c$—*, *—$CH_2CH_2$—*, *—C(=O)$O^-N^+(R^d)_3$—*, *—$SO_3^-N^+(R^e)_3$—*, and *—$PO_3H^-N^+(R^f)_3$—* where M represents a divalent to tetravalent metal atom; $R^a$, $R^b$, $R^c$, $R^d$, $R^e$, and $R^f$ each independently represent a hydrogen atom or an alkyl group; and the symbol * represents a linking site.

The metal atom M is preferably a metal atom selected from the group consisting of Be, Mg, Ca, Sc, Y, Ti, Zr, V, Cr, Mo, Mn, Fe, Co, Ni, Cu, Zn, B, Al, Ga, and In.

General formula (VI)

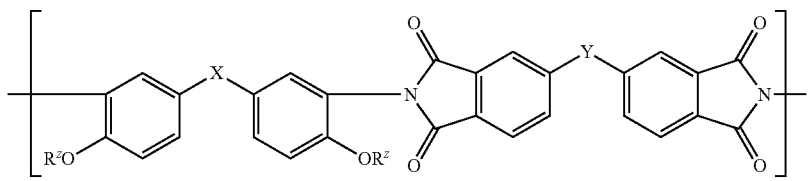

General formula (VII)

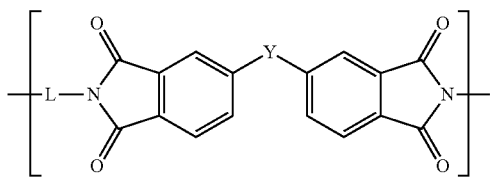

The siloxane compound layer preferably has at least one structure represented by (a) or (b).

(a) A structure having a structure represented by General formula (1) and a structure represented by General formula (2) or General formula (3)

(b) A structure represented by General formula (4)

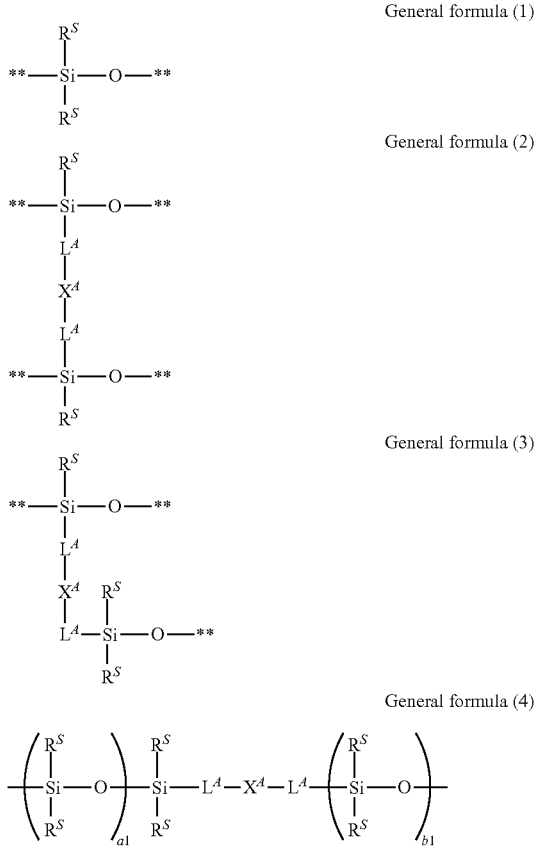

General formula (1)

General formula (2)

General formula (3)

General formula (4)

In the formulae, $R^S$ represents an alkyl group or an aryl group; $L^A$ represents a single bond or a divalent linking group; $X^A$ represents a linking group selected from the group consisting of *—O-$M^1$-O—*, *—S-$M^1$-S—*, *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—* where $M^1$ represents Zr, Fe, Zn, B, Al, Ti, In, or Ga; $R^d$ represents a hydrogen atom or an alkyl group; a1 and b1 are each an integer of 2 or more; the symbol * represents a linking site; and the symbol ** represents a linking site in a siloxane bond.

The structure of (a) preferably further has a repeating unit represented by Formula (5).

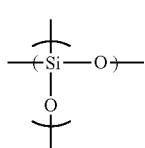

Formula (5)

A content ratio of the repeating unit represented by Formula (5) in the siloxane compound layer is preferably 0.01 to 0.55.

The gas separation membrane is preferably used for selectively allowing permeation of carbon dioxide from gas containing carbon dioxide and methane.

A second aspect of the present invention provides a gas separation module including the gas separation membrane according to the first aspect.

A third aspect of the present invention provides a gas separation apparatus including the gas separation module according to the second aspect.

A fourth aspect of the present invention provides a gas separation method including using the gas separation membrane according to the first aspect.

The gas separation method according to the fourth aspect preferably includes selectively allowing permeation of carbon dioxide from gas containing carbon dioxide and methane.

Herein, when a plurality of substituents, linking groups, or the like (hereinafter referred to as substituents or the like) represented by specific symbols are present or a plurality of substituents or the like are defined simultaneously or alternatively, the substituents or the like may be the same or different from each other. The same applies to the definition of the number of substituents or the like. When a formula includes a plurality of repeated partial structures represented by the same expression, the partial structures or the repeating units may be the same or different from each other. In addition, even if not specifically stated, when a plurality of substituents or the like are close to each other, they may be linked or fused to each other to form a ring.

With regard to expressing compounds used herein, the expression includes salts thereof and ions thereof in addition to the compounds.

Herein, a substituent (the same applies to a linking group) in which substitution or no substitution is not specified may have any substituent within the range in which desired effects are achieved. The same applies to a compound in which substitution or no substitution is not specified.

The gas separation membrane, the gas separation module, and the gas separation apparatus of the present invention realize both gas permeability and gas separation selectivity at a high level. The gas separation membrane of the present invention is unlikely to be plasticized, even in the presence of impurities such as toluene, exhibits good gas separation performance, even under high-temperature, high-pressure, and high-humidity conditions, exhibits good folding endurance, and can be produced at a high yield. According to the gas separation method of the present invention, gas can be separated with higher permeability and higher selectivity. Furthermore, even when gas is separated under high-pressure conditions or impurities such as toluene are present in gas, high gas separation performance is maintained.

DESCRIPTION OF THE PREFERRED EMBODIMENTS

Figure 1:
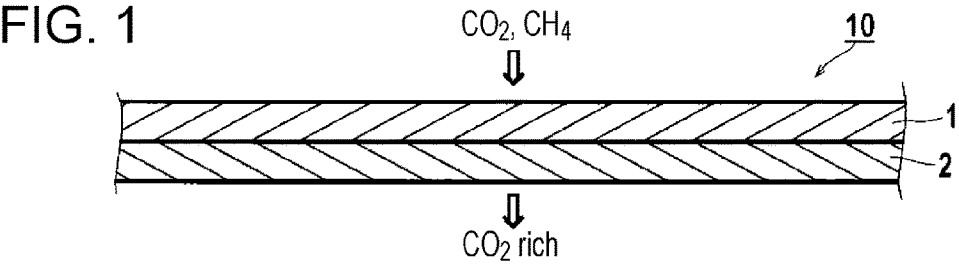
FIG. 1 is a schematic sectional view illustrating a gas separation membrane according to an embodiment (composite membrane) of the present invention.

The present invention will now be described in detail.

A gas separation membrane of the present invention has a gas separation layer containing a poly(benzoxazole-imide) compound having a particular structure. The gas separation membrane of the present invention may have a form of a composite membrane or a form of an asymmetric membrane.

Poly(Benzoxazole-Imide) Compound

The poly(benzoxazole-imide) compound that forms the gas separation layer of the present invention satisfies a condition (A) or (B).

(A) The poly(benzoxazole-imide) compound has a structural unit represented by General formula (I) and a structural unit represented by General formula (II), and in the poly(benzoxazole-imide) compound, a molar quantity m of the structural unit represented by General formula (I) and a molar quantity n of the structural unit represented by General formula (II) satisfy Mathematical expression 1.

(B) The poly(benzoxazole-imide) compound has the structural unit represented by General formula (I), the structural unit represented by General formula (II), and a structural unit represented by General formula (III), and in the poly(benzoxazole-imide) compound, the molar quantity m of the structural unit represented by General formula (I), the molar quantity n of the structural unit represented by General formula (II), and a molar quantity q of the structural unit represented by General formula (III) satisfy Mathematical expression 2.

$0.25 \leq m/n \leq 9.00 (0<n)$      Mathematical expression 1:

$0.25 \leq m/(n+q) \leq 9.00 (0<n, 0<q)$      Mathematical expression 2:

In General formulae (I) to (III), X and Y each represent a single bond, a divalent linking group selected from Group (IV), or a divalent linking group formed by combining one or two or more linking groups selected from the following Group (IV).

Group (IV)

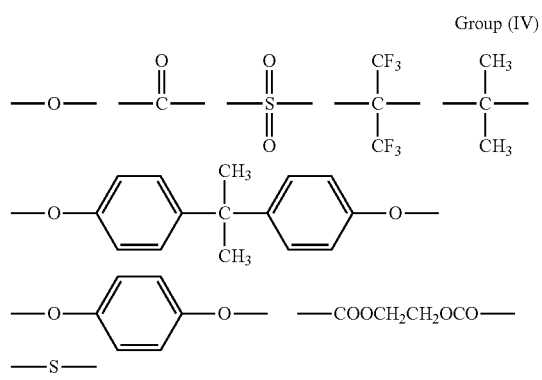

X is preferably a single bond or a divalent linking group selected from Group (IV), and more preferably a single bond or a divalent linking group represented by the following formula.

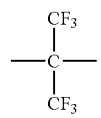

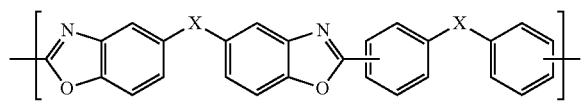

General formula (I)

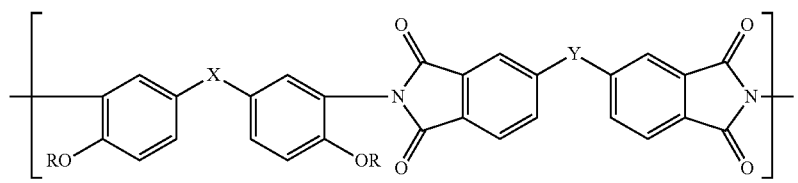

General formula (II)

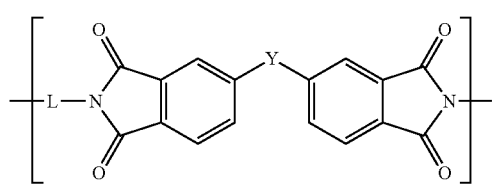

General formula (III)

Y is preferably a single bond or a divalent linking group selected from Group (IV), more preferably a single bond or a divalent linking group selected from Group (IV-1), and still more preferably a divalent linking group selected from the following Group (IV-2).

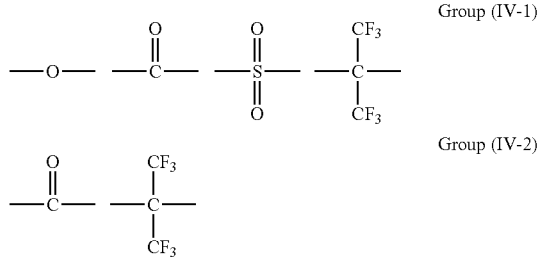

Y is particularly preferably a divalent linking group represented by the following formula.

In General formula (II), each R represents H, $COR^1$, or $Si(R^2)_3$ where $R^1$ and $R^2$ each represent an alkyl group.

The alkyl groups for $R^1$ and $R^2$ preferably have 1 to 10 carbon atoms, more preferably have 1 to 6 carbon atoms, and still more preferably have 1 to 4 carbon atoms. These alkyl groups may be linear or branched. Specific examples of the alkyl groups include methyl, ethyl, isopropyl, n-butyl, t-butyl, pentyl, hexyl, heptyl, octyl, and 1-ethylpentyl. Of these, methyl or t-butyl is preferable.

R is preferably H or $COR^1$, more preferably H or $COCH_3$, and still more preferably H.

In General formula (III), L represents a divalent linking group having a phenylene group provided that this phenylene group does not have an —OR group as a substituent. Here, the —OR group has the same definition as the —OR group in General formula (II). Specifically, the phenylene group for L does not have —OH, —$OCOR^1$, or —$OSi(R^2)_3$ as a substituent where $R^1$ and $R^2$ have the same definition as $R^1$ and $R^2$ in General formula (II).

L is preferably a divalent linking group selected from the following Group (V) of linking groups.
Group (V) of Linking Groups

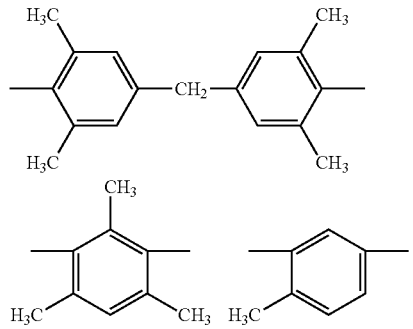

L is more preferably a divalent linking group represented by the following formula.

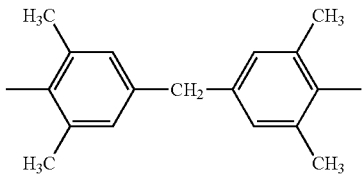

In the poly(benzoxazole-imide) compound that forms the gas separation layer of the present invention, a molar quantity m of the structural unit represented by General formula (I), a molar quantity n of the structural unit represented by General formula (II), and a molar quantity q of the structural unit represented by General formula (III), the structural units being present in the poly(benzoxazole-imide) compound, satisfy the following mathematical expression.

$$0.25 \leq m/(n+q) \leq 9.00 (0 < n, 0 \leq q)$$

In the poly(benzoxazole-imide) compound, the molar ratio (i.e., the molar ratio of m, n, and q described above) of the structural units represented by General formulae (I) to (III) can be determined by X-ray photoelectron spectroscopy (XPS). More specifically, the molar ratio can be determined by XPS analysis in accordance with the method described in Journal of Membrane Science, 2012, Vol. 397-398, pp. 51-65.

From the viewpoint of, for example, impurity resistance, m, n, and q preferably satisfy $0.30 \leq m/(n+q) \leq 7.00$, more preferably $0.35 \leq m/(n+q) \leq 5.00$, still more preferably $0.40 \leq m/(n+q) \leq 3.00$, and particularly preferably $0.40 \leq m/(n+q) \leq 1.60$.

When $m/(n+q)$ is less than 0.25, a reduction in the density due to the conversion from polyimide to polybenzoxazole and thermal crosslinking are insufficient, and it becomes difficult to enhance gas permeance and impurity resistance (plasticization resistance) to desired levels. When $m/(n+q)$ is more than 9.00, it becomes difficult to obtain sufficient separation selectivity, membrane formability, and folding endurance because of an excessive reduction in the density and an excessive progress of thermal crosslinking.

In the poly(benzoxazole-imide) compound, the molar quantity q of the structural unit represented by General formula (III) preferably satisfies $0<q$. That is, the poly(benzoxazole-imide) compound preferably satisfies (B) described above. In the poly(benzoxazole-imide) compound, the ratio of the molar quantity n of the structural unit represented by General formula (II) to the molar quantity q of the structural unit represented by General formula (III) is preferably n/q=0.1 to 50, and more preferably n/q=0.2 to 20.

In the poly(benzoxazole-imide) compound, the total of the structural units represented by General formulae (I) to (III) is preferably 90% by mass or more, more preferably 95% by mass or more, and still more preferably 97% by mass or more.

Herein, the poly(benzoxazole-imide) compound may form a crosslinked structure in the gas separation layer. For example, when the poly(benzoxazole-imide) compound has —$SO_2$— or —CO— as X or Y, the —$SO_2$— or —CO— becomes a radical, which is capable of causing a crosslinking reaction, when being subjected to ultraviolet irradiation or heat treatment.

Preparation of Poly(Benzoxazole-Imide) Compound

In the present invention, the poly(benzoxazole-imide) compound contained in the gas separation layer can be synthesized by, for example, heat-treating a polyimide compound having a structural unit represented by General formula (VI) and a structural unit represented by General formula (VII) to convert the polyimide compound to a poly(benzoxazole-imide) compound.

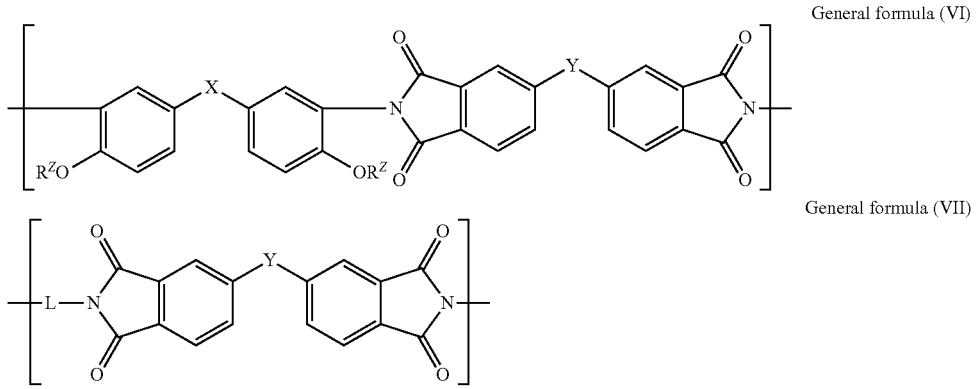

General formula (VI)

General formula (VII)

A possible reaction scheme in which the polyimide compound is converted to a poly(benzoxazole-imide) compound by heat treatment is shown below. However, the reaction scheme shown below is merely an assumption, and the present invention is not limited to this reaction scheme. Specifically, the synthesis may be performed through any reaction as long as $CO_2$ and $R^Z$—OH are eliminated to produce a poly(benzoxazole-imide) compound after heat treatment. In the scheme below, the wavy line shown on the left side represents a site linking to Y, and the wavy line shown on the right side represents a site linking to X.

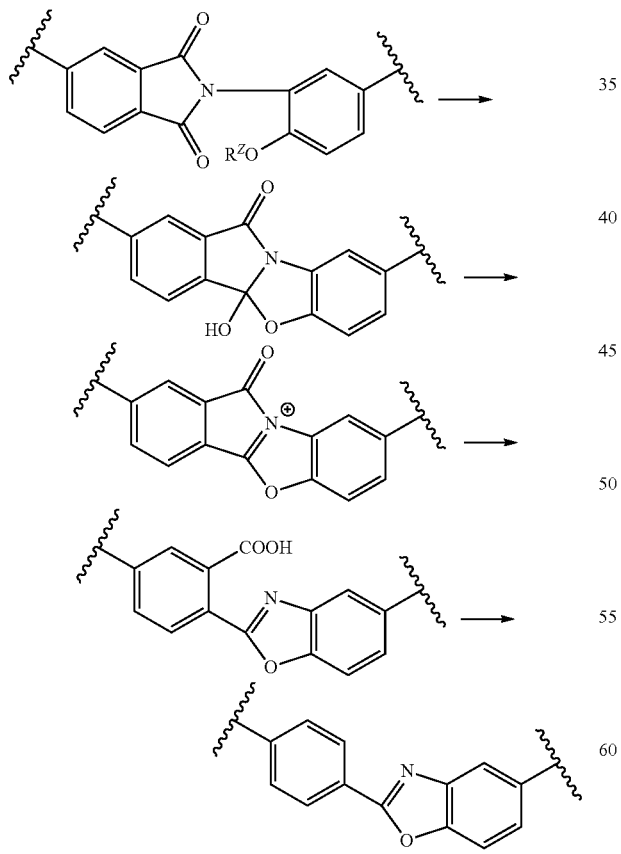

In General formulae (VI) and (VII), X, Y, and L respectively have the same definition as X, Y, and L in General formulae (II) and (III), and the preferred forms of X, Y, and L are also the same as those of X, Y, and L in General formulae (II) and (III).

In General formula (VI), $R^Z$ represents H, $COR^1$, or $Si(R^2)_3$ where $R^1$ and $R^2$ respectively have the same definition as $R^1$ and $R^2$ in General formula (II), and the preferred forms of $R^1$ and $R^2$ are also the same as those of $R^1$ and $R^2$ in General formula (II).

$R^Z$ is preferably $COR^1$ or $Si(R^2)_3$, and more preferably $COCH_3$.

The temperature of heat-treating (heat-treatment temperature) during the conversion of the polyimide compound to the poly(benzoxazole-imide) compound is usually 300° C. to 600° C., and preferably 350° C. to 450° C. Conversion to the poly(benzoxazole-imide) compound having the structural unit ratio described above can be achieved by appropriately adjusting the heat-treatment temperature and the heat-treatment time. The heat-treatment time is usually 0.5 to 3 hours.

Synthesis of Polyimide Compound

The polyimide compound used as a precursor of the poly(benzoxazole-imide) compound can be synthesized by polycondensation of a particular bifunctional acid anhydride (tetracarboxylic dianhydride) and a particular diamine. For example, a method described in "The Latest Polyimide, —Fundamentals and Applications-" written and edited by Yoshio Imai and Rikio Yokota, published by NTS Inc., Aug. 25, 2010, pp. 3 to 49 is suitable for the method for synthesizing the polyimide compound.

For example, in the synthesis of the polyimide compound, the structural unit represented by General Formula (VI) is formed by a polycondensation reaction of a diamine compound represented by Formula (VI-a) and a tetracarboxylic dianhydride represented by Formula (VI-b).

General formula (VI-a)

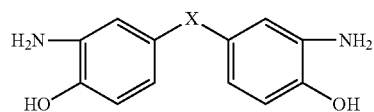

-continued

General formula (VI-b)

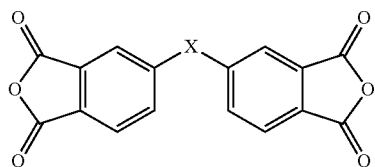

In the polycondensation reaction, —OH can be changed to —OR$^Z$ (where R$^Z$ used herein is not H) by using a specific condensing agent, as described below.

Similarly, in the synthesis of the polyimide compound, the structural unit represented by Formula (VII) is formed by a polycondensation reaction of a diamine compound represented by Formula (VII-a) and a tetracarboxylic dianhydride represented by Formula (VII-b).

General formula (VII-a)

H$_2$N—L—NH$_2$

General formula (VII-b)

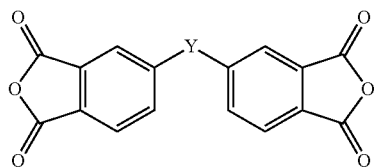

Examples of the solvents used in the synthesis of the polyimide compound include, but are not particularly limited to, ester organic solvents such as methyl acetate, ethyl acetate, and butyl acetate; aliphatic ketones such as acetone, methyl ethyl ketone, methyl isobutyl ketone, diacetone alcohol, cyclopentanone, and cyclohexanone; ether organic solvents such as ethylene glycol dimethyl ether, dibutyl ether, tetrahydrofuran, methyl cyclopentyl ether, and dioxane; amide organic solvents such as N-methylpyrrolidone, 2-pyrrolidone, dimethylformamide, dimethylimidazolidinone, and dimethylacetamide; and sulfur-containing organic solvents such as dimethyl sulfoxide and sulfolane. These organic solvents are appropriately selected in a range where a tetracarboxylic dianhydride and a diamine compound, which are reaction substrates, a polyamic acid, which is a reaction intermediate, and a polyimide compound, which is a final product, can be dissolved. Esters (preferably, butyl acetate), aliphatic ketones (preferably, methyl ethyl ketone, methyl isobutyl ketone, diacetone alcohol, cyclopentanone, and cyclohexanone), ethers (diethylene glycol monomethyl ether and methyl cyclopentyl ether), amides (preferably, N-methylpyrrolidone), and sulfur-containing solvents (dimethyl sulfoxide and sulfolane) are preferable. These solvents may be used alone or in combination of two or more thereof.

The temperature of the polycondensation reaction is not particularly limited and may be a temperature usually used in the synthesis of polyimide compounds. In particular, in order to obtain a polyimide compound having a high degree of polymerization and high strength, it is preferable to mix the materials at a low temperature and cause a polymerization reaction. This synthesis reaction will be described below.

Step of Mixing Tetracarboxylic Dianhydride and Diamine Compound

The temperature during mixing of (in a step of mixing) a tetracarboxylic dianhydride and a diamine, which are reaction substrates, is preferably lower than 0° C. The lower limit of the temperature is not particularly limited and can be appropriately set in consideration of, for example, freezing of the solvent and reactivity. Nevertheless, considering the production cost and reaction efficiency, the temperature in a polymerization initiation step is preferably −78° C. or higher and lower than −5° C., more preferably −40° C. or higher and lower than −10° C., and still more preferably −20° C. or higher and lower than −10° C. The means for mixing is not particularly limited, but preferably, a powder or a solution of a diamine or a tetracarboxylic dianhydride is added to and mixed with a solution of a tetracarboxylic dianhydride or a solution of a diamine. In a typical polymerization reaction of polyimide, in consideration of hydrolysis of a tetracarboxylic dianhydride due to moisture absorption, a method of adding a tetracarboxylic dianhydride to a solution of a diamine is considered to be preferable. However, in the production method of the present invention, hydrolysis of a tetracarboxylic dianhydride is significantly reduced because a low-temperature mixing, which has not hitherto been used, is employed. Accordingly, in the production method of the present invention, it is also possible to employ a method of adding a powder or a solution of a diamine dropwise in a solution of a tetracarboxylic dianhydride.

Polymerization Reaction Step (Aging Step)

The low-temperature mixing of a tetracarboxylic dianhydride and a diamine compound described above produces a low-molecular weight polyamic acid, which is a reaction intermediate, in the mixed liquid. In order to obtain a polyamic acid having a desired high degree of polymerization, it is necessary to cause a polymerization reaction to proceed (to be aged). The temperature in this step is not particularly limited and may be a temperature of lower than 0° C., which is the temperature during mixing. However, in order to reduce the time of the aging step, a higher temperature is preferred. On the other hand, when the temperature in the aging step is excessively high, decomposition of the polyamic acid due to a side reaction occurs, resulting in a decrease in the degree of polymerization. In view of these points, the temperature in the aging step is preferably 0° C. or higher and lower than 80° C., more preferably 5° C. or higher and lower than 60° C., and still more preferably 10° C. or higher and lower than 40° C.

The time of the aging step is not particularly limited. However, the polyamic acid decomposes with time, and therefore, aging for a long time is not desirable. The time of the aging step is preferably 1 hour or more and 72 hours or less, more preferably 2 hours or more and 48 hours or less, and still more preferably 3 hours or more and 24 hours or less. In the case where the reaction product must be stored in the form of a polyamic acid, the polyamic acid is preferably stored in an inert gas atmosphere at a low temperature.

Imidization Step

A polyimide compound is obtained by imidizing the polyamic acid, which is generated by the polymerization reaction, through a dehydration ring-closure reaction in a molecule. Examples of the imidization method that can be employed include a thermal imidization method of causing a reaction while heating in a range of 120° C. to 200° C. to remove water generated as a by-product to the outside of the system, and a so-called chemical imidization method in which a dehydration condensing agent such as acetic anhydride, dicyclohexylcarbodiimide, or triphenyl phosphite is used in the coexistence of a basic catalyst such as pyridine, triethylamine, or diazabicycloundecene (DBU). For example, when $R^Z$ in General formula (VI) is a hydrogen atom, the thermal imidization method is preferably employed. When $R^Z$ is —COCH$_3$, a method of imidization using acetic anhydride or a method in which imidization is performed by the thermal imidization method and —OH is subsequently converted to —COCH$_3$ with acetic anhydride or the like may be employed.

The concentration of the tetracarboxylic dianhydride and the diamine compound in the reaction mixture in the polycondensation reaction is not particularly limited, but is preferably 5% to 70% by mass, more preferably 5% to 50% by mass, and still more preferably 5% to 30% by mass.

The molecular weight of the polyimide compound is, in terms of weight-average molecular weight, preferably 10,000 to 1,000,000, more preferably 15,000 to 500,000, still more preferably 20,000 to 200,000, even still more preferably 50,000 to 200,000, even still more preferably 80,000 to 200,000, even still more preferably 100,000 to 250,000, even still more preferably 120,000 to 250,000, and particularly preferably 140,000 to 230,000.

The terms "molecular weight" and "dispersity" used herein refer to values determined by gel permeation chromatography (GPC) unless otherwise stated, and the term "molecular weight" refers to a weight-average molecular weight in terms of polystyrene. A gel filling a column used for GPC is preferably a gel having an aromatic compound as a repeating unit. An example thereof is a gel formed of a styrene-divinylbenzene copolymer. Preferably, two to six columns are connected together and used. Examples of the solvent used include ether solvents such as tetrahydrofuran and amide solvents such as N-methylpyrrolidinone. The measurement is preferably conducted with a solvent flow velocity in the range of 0.1 to 2 mL/min, and most preferably in the range of 0.5 to 1.5 mL/min. When the measurement is conducted in this range, a load is not applied to the apparatus and the measurement can be conducted more efficiently. The measurement temperature is preferably 10° C. to 50° C., and most preferably 20° C. to 40° C. The column and the carrier used can be appropriately selected in accordance with physical properties of a polymer compound to be measured.

A method for forming a gas separation layer that contains the poly(benzoxazole-imide) compound using the polyimide compound will be described later.

Siloxane Compound Layer

In the gas separation membrane of the present invention, a siloxane compound layer is preferably provided as a protective layer on the gas separation layer so as to be in contact with the gas separation layer. The term "siloxane compound" used herein refers to an organopolysiloxane compound unless otherwise stated.

The siloxane compound layer preferably has a Si ratio in the range of 0.6 to 1.0, the Si ratio being a Si ratio of the siloxane compound layer after immersion in chloroform to the siloxane compound layer before immersion in chloroform and represented by Mathematical expression (I).

Si ratio=(Si–KαX-ray intensity after immersion in chloroform)/(Si–KαX-ray intensity before immersion in chloroform)  Mathematical expression (I)

The Si ratio is determined by irradiating a surface of a siloxane compound layer with X-rays before and after immersion of the siloxane compound layer in chloroform at 25° C. for 12 hours, and measuring the intensity of a peak (2θ=144.6 degrees) of the Si–Kα X-ray (1.74 keV). The method for measuring the Si–Kα X-ray intensity is described in, for example, Japanese Unexamined Patent Application Publication No. 6-88792. A decrease in the Si–Kα X-ray intensity after immersion in chloroform compared with the Si–Kα X-ray intensity before the immersion means that a low-molecular weight component is present and this component has dissolved into chloroform. Accordingly, a lower degree of the decrease in the Si–Kα X-ray intensity after immersion in chloroform means that the polymer constituting the siloxane compound layer is more highly polymerized and less likely to be dissolved into chloroform.

When the Si ratio of the siloxane compound layer is in the range of 0.6 to 1.0, a siloxane compound can be made present at a high density and homogeneously, membrane defects can be effectively prevented, and the gas separation performance can be further enhanced. Furthermore, it becomes possible to use the membrane under high-pressure, high-temperature, and high-humidity conditions and to further suppress plasticization of the gas separation layer due to an impurity component such as toluene.

The Si ratio of the siloxane compound layer in the present invention is preferably 0.7 to 1.0, more preferably 0.75 to 1.0, still more preferably 0.8 to 1.0, and particularly preferably 0.85 to 1.0.

The siloxane compound layer in the present invention preferably contains an organopolysiloxane compound having a structure in which siloxane compounds are linked to each other through a linking group selected from the group consisting of *—O-M-O—*, *—S-M-S—*, *—NR$^a$C (=O)—*, *—NR$^b$C(=O)NR$^b$—*, *—O—CH$_2$—O—*, *—S—CH$_2$CH$_2$—*, *—OC(=O)O—*, *—CH(OH) CH$_2$OCO—*, *—CH(OH)CH$_2$O—*, *—CH(OH)CH$_2$S— *, *—CH(OH)CH$_2$NR$^c$—*, *—CH(CH$_2$OH)CH$_2$OCO—*, —CH(CH$_2$OH)CH$_2$O—*, —CH(CH$_2$OH)CH$_2$S—*, *—CH(CH$_2$OH)CH$_2$N(R$^c$)—*, *—CH$_2$CH$_2$—*, *—C (=O)O$^-$N$^+$(R$^d$)$_3$—*, *—SO$_3^-$N$^+$(R$^e$)$_3$—*, and *—PO$_3$H$^-$ N$^+$(R$^f$)$_3$—*.

In the formulae, M represents a divalent to tetravalent metal atom; $R^a$, $R^b$, $R^c$, $R^d$, $R^e$, and $R^f$ each independently represent a hydrogen atom or an alkyl group; and the symbol * represents a linking site.

Examples of the metal atom M include metal atoms selected from the group consisting of aluminum (Al), iron (Fe), beryllium (Be), gallium (Ga), vanadium (V), indium (In), titanium (Ti), zirconium (Zr), copper (Cu), cobalt (Co), nickel (Ni), zinc (Zn), calcium (Ca), magnesium (Mg), yttrium (Y), scandium (Sc), chromium (Cr), manganese (Mn), molybdenum (Mo), and boron (B). Of these, a metal atom selected from Ti, In, Zr, Fe, Zn, Al, Ga, and B is preferable, a metal atom selected from Ti, In, and Al is more preferable, and Al is still more preferable.

The alkyl groups for $R^a$, $R^b$, $R^c$, $R^d$, $R^e$, and $R^f$ are preferably alkyl groups having 1 to 20 carbon atoms, more preferably alkyl groups having 1 to 10 carbon atoms, still more preferably alkyl groups having 1 to 7 carbon atoms, and particularly preferably alkyl groups having 1 to 4 carbon atoms. These alkyl groups may be linear or branched, and are more preferably linear. Specific preferred examples of the alkyl groups include methyl, ethyl, isopropyl, n-butyl, t-butyl, pentyl, hexyl, heptyl, octyl, and 1-ethylpentyl.

When the siloxane compound layer has a structure in which siloxane compounds are linked to each other through the above linking group, the Si ratio of the siloxane compound layer can be more easily increased to the range specified in the present invention.

Reactions in which siloxane compounds are linked to each other through the linking group will be described below.

The linking group *—O-M-O—* can be formed by, for example, a ligand exchange reaction between a siloxane compound having a group having —OH (active hydrogen-containing group), such as a hydroxy group, a carboxy group, or a sulfo group and a metal complex (crosslinking agent) represented by Formula (B) below.

$$M{-\!\!\!+\!\!\!-}(L^L)_y \tag{B}$$

In the formula, M has the same definition as the above metal atom M, and the preferred form of M is also the same as that of the metal atom M; $L^L$ represents an alkoxy group, an aryloxy group, an acetylacetonato group, an acyloxy group, a hydroxy group, or a halogen atom; and y represents an integer of 2 to 4.

The alkoxy group for $L^L$ is preferably an alkoxy group having 1 to 10 carbon atoms, more preferably an alkoxy group having 1 to 4 carbon atoms, and still more preferably an alkoxy group having 1 to 3 carbon atoms. Specific examples of the alkoxy group for $L^L$ include methoxy, ethoxy, tert-butoxy, and isopropoxy.

The aryloxy group for $L^L$ is preferably an aryloxy group having 6 to 10 carbon atoms, more preferably an aryloxy group having 6 to 8 carbon atoms, and still more preferably an aryloxy group having 6 to 7 carbon atoms. Specific examples of the aryloxy group for $L^L$ include phenoxy, 4-methoxyphenoxy, and naphthoxy.

The acyloxy group for $L^L$ is preferably an acyloxy group having 2 to 10 carbon atoms, more preferably an acyloxy group having 2 to 6 carbon atoms, and still more preferably an acyloxy group having 2 to 4 carbon atoms. Specific examples of the acyloxy group for $L^L$ include acetoxy, propanoyloxy, pivaloyloxy, and acetyloxy.

Examples of the halogen atom for $L^L$ include, but are not particularly limited to, a fluorine atom, a chlorine atom, a bromine atom, and an iodine atom. Of these, a chlorine atom is preferred.

The metal complex represented by Formula (B) is preferably soluble in an organic solvent used in a coating solution for forming the siloxane compound layer. More specifically, the degree of solubility of the metal complex represented by Formula (B) in 100 g of tetrahydrofuran at 25° C. is preferably 0.01 to 10 g, and more preferably 0.1 to 1.0 g. When the metal complex represented by Formula (B) is soluble in the organic solvent, a more homogeneous metal-crosslinked siloxane compound layer can be formed.

Specific preferred examples of the metal complex represented by Formula (B) include metal complexes selected from aluminum acetylacetonate, gallium acetylacetonate, indium acetylacetonate, zirconium acetylacetonate, cobalt acetylacetonate, calcium acetylacetonate, nickel acetylacetonate, zinc acetylacetonate, magnesium acetylacetonate, ferric chloride, copper(II) acetate, aluminum isopropoxide, titanium isopropoxide, boric acid, and boron trifluoride-diethyl ether complex.

An example of the ligand exchange reaction is shown below. The example shown below illustrates a case where the siloxane compound has a hydroxy group. In the case where the siloxane compound has another active hydrogen-containing group such as a carboxy group or a sulfo group, a similar ligand exchange reaction proceeds to form the linking group represented by *—O-M-O—*.

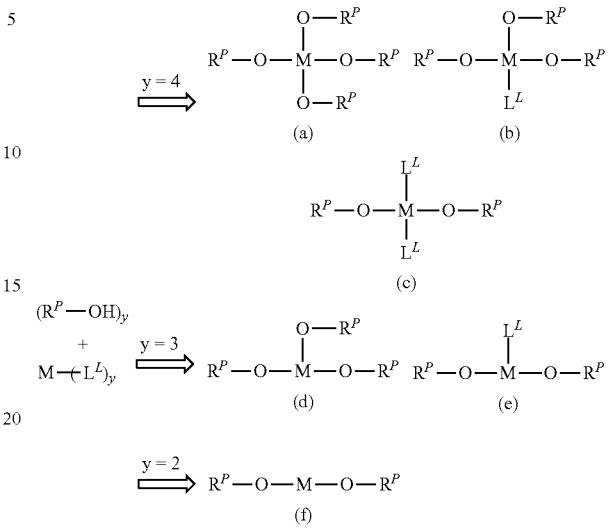

In the formulae, $R^P$ represents a siloxane compound residue (that is, $R^P$—OH represents a siloxane compound having a hydroxy group).

When M is a tetravalent metal atom (y=4), at most four $R^P$—OH can usually coordinate to one M (the form of (a) above). In the present invention, when M is a tetravalent metal atom, all of the form in which two $R^P$—OH coordinate (the form of (c) above), the form in which three $R^P$—OH coordinate (the form of (b) above), and the form in which four $R^P$—OH coordinate (the form of (a) above) are considered to be included in the form having the linking group represented by *—O-M-O—*.

Although not shown in the above formulae, when the siloxane compound $R^P$—OH is represented by $R^{P1}$—(OH)$_h$ (where $R^{P1}$ represents a siloxane compound residue and h represents an integer of 2 or more, that is, in the case of a form having two or more hydroxy groups in one molecule), two or more OH present in one molecule of $R^{P1}$—(OH)$_h$ may coordinate to one M. This form is also considered to be included in the form having the linking group represented by *—O-M-O—*.

When M is a trivalent metal atom (y=3), at most three $R^P$—OH can usually coordinate to one M (the form of (d) above). In the present invention, when M is a trivalent metal atom, both the form in which two $R^P$—OH coordinate (the form of (e) above) and the form in which three $R^P$—OH coordinate (the form of (d) above) are considered to be included in the form having the linking group represented by *—O-M-O—*.

Although not shown in the above formulae, when the siloxane compound $R^P$—OH is represented by $R^{P1}$—(OH)$_h$ (where $R^{P1}$ represents a siloxane compound residue and h represents an integer of 2 or more, that is, in the case of a form having two or more hydroxy groups in one molecule), two or more OH present in one molecule of $R^{P1}$—(OH)$_h$ may coordinate to one M. This form is also considered to be included in the form having the linking group represented by *—O-M-O—*.

When M is a divalent metal atom (y=2), the form of (f) above is the form having the linking group represented by *—O-M-O—* and specified in the present invention.

Although not shown in the above formula, when the siloxane compound $R^P$—OH is represented by $R^{P1}$—$(OH)_h$ (where $R^{P1}$ represents a siloxane compound residue and h represents an integer of 2 or more, that is, in the case of a form having two or more hydroxy groups in one molecule), two or more OH present in one molecule of $R^{P1}$—$(OH)_h$ may coordinate to one M. This form is also considered to be included in the form having the linking group represented by *—O-M-O—*.

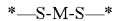

The linking group *—S-M-S—* can be formed by, for example, a ligand exchange reaction between a siloxane compound having a thiol group and a metal complex represented by Formula (B) above. This reaction includes a reaction form in which $R^P$—OH in the above-described reaction for forming *—O-M-O—* is replaced by $R^P$—SH. Since —SH is also an active hydrogen-containing group, the ligand exchange reaction can be performed in the same manner as described above.

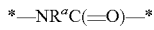

The linking group *—$NR^aC(=O)$—* can be formed by, for example, allowing a siloxane compound having a carboxy group and a siloxane compound having an amino group to react with each other in the presence of a dehydration condensing agent (for example, a carbodiimide compound). This reaction can be represented by the following formula.

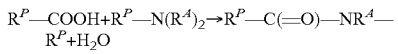

In the formula, $R^P$ represents a siloxane compound residue. Of the two $R^A$ linked to one N on the left side, one $R^A$ is a hydrogen atom and the other $R^A$ is a hydrogen atom or an alkyl group (that is, $R^A$ on the right side is a hydrogen atom or an alkyl group).

Alternatively, the above linking group can be forming by allowing a siloxane compound having a carboxy group and a compound having two or more amino groups and functioning as a crosslinking agent to react with each other. Alternatively, the above linking group can be formed by allowing a siloxane compound having an amino group and a compound having two or more carboxy groups and functioning as a crosslinking agent to react with each other.

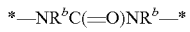

The linking group *—$NR^bC(=O)NR^b$—* can be formed by, for example, allowing a siloxane compound having an amino group and a chloroformate functioning as a crosslinking agent to react with each other. This reaction can be represented by the following formula.

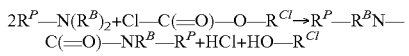

In the formula, $R^P$ represents a siloxane compound residue, and $R^{Cl}$ represents an alcohol residue of a chloroformate. Of the two $R^B$ linked to one N on the left side, one $R^B$ is a hydrogen atom and the other $R^B$ is a hydrogen atom or an alkyl group (that is, each $R^B$ on the right side is a hydrogen atom or an alkyl group).

The linking group *—O—$CH_2$—O—* can be formed by, for example, allowing a siloxane compound having a hydroxy group and formaldehyde functioning as a crosslinking agent to react with each other. This reaction can be represented by the following formula.

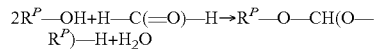

In the formula, $R^P$ represents a siloxane compound residue.

The linking group *—S—$CH_2CH_2$—* can be formed by, for example, allowing a siloxane compound having a thiol group and a siloxane compound having a vinyl group to react with each other. This reaction can be represented by the following formula.

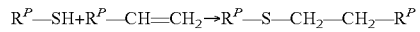

In the formula, $R^P$ represents a siloxane compound residue.

Alternatively, the above linking group can be formed by allowing a siloxane compound having a thiol group and a compound having two or more vinyl groups and functioning as a crosslinking agent to react with each other. Alternatively, the above linking group can be formed by allowing a siloxane compound having a vinyl group and a compound having two or more thiol groups and functioning as a crosslinking agent to react with each other.

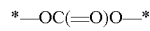

The linking group *—OC(=O)O—* can be formed by, for example, allowing a siloxane compound having a hydroxy group and a chloroformate functioning as a crosslinking agent to react with each other. This reaction can be represented by the following formula.

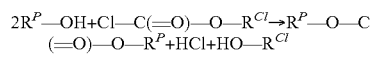

In the formula, $R^P$ represents a siloxane compound residue, and $R^{Cl}$ represents an alcohol residue of a chloroformate.

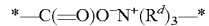

The linking group *—$C(=O)O^-N^+(R^d)_3$—* can be formed by, for example, allowing a siloxane compound having a carboxy group and a siloxane compound having an amino group to react with each other. This reaction can be represented by the following formula.

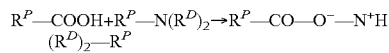

In the formula, $R^P$ represents a siloxane compound residue, and $R^D$ represents a hydrogen atom or an alkyl group.

Alternatively, the above linking group can be formed by allowing a siloxane compound having a carboxy group and a compound having two or more amino groups and functioning as a crosslinking agent to react with each other. Alternatively, the above linking group can be formed by allowing a siloxane compound having an amino group and a compound having two or more carboxy groups and functioning as a crosslinking agent to react with each other.

The linking group *—$SO_3^-N^+(R^e)_3$—* can be formed by, for example, allowing a siloxane compound having a sulfo group and a siloxane compound having an amino group to react with each other. This reaction can be represented by the following formula.

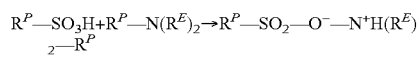

In the formula, $R^P$ represents a siloxane compound residue, and $R^E$ represents a hydrogen atom or an alkyl group.

Alternatively, the above linking group can be formed by allowing a siloxane compound having a sulfo group and a compound having two or more amino groups and functioning as a crosslinking agent to react with each other. Alternatively, the above linking group can be formed by allowing a siloxane compound having an amino group and a compound having two or more sulfo groups and functioning as a crosslinking agent to react with each other.

$*-PO_3H^-N^+(R^f)_3-*$

The linking group $*-PO_3H^-N^+(R^f)_3-*$ can be formed by, for example, allowing a siloxane compound having a phosphonic acid group and a siloxane compound having an amino group to react with each other. This reaction can be represented by the following formula.

$$R^P-PO_3H_2+R^P-N(R^F)_2 \rightarrow R^P-P(=O)(OH)-O^--N^+H(R^F)_2-R^P$$

In the formula, $R^P$ represents a siloxane compound residue, and $R^F$ represents a hydrogen atom or an alkyl group.

Alternatively, the above linking group can be formed by allowing a siloxane compound having a phosphonic acid group and a compound having two or more amino groups and functioning as a crosslinking agent to react with each other. Alternatively, the above linking group can be formed by allowing a siloxane compound having an amino group and a compound having two or more phosphonic acid groups and functioning as a crosslinking agent to react with each other.

$*-CH(OH)CH_2OCO-*$

The linking group $-CH(OH)CH_2OCO-*$ can be formed by, for example, allowing a siloxane compound having an epoxy group and a siloxane compound having a carboxy group to react with each other.

Alternatively, the above linking group can be formed by allowing a siloxane compound having an epoxy group and a compound having two or more carboxy groups and functioning as a crosslinking agent to react with each other. Alternatively, the above linking group can be formed by allowing a siloxane compound having a carboxy group and a compound having two or more epoxy groups and functioning as a crosslinking agent to react with each other.

$*-CH(OH)CH_2O-*$

The linking group $*-CH(OH)CH_2O-*$ can be formed by, for example, allowing a siloxane compound having an epoxy group and a siloxane compound having a hydroxy group to react with each other.

Alternatively, the above linking group can be formed by allowing a siloxane compound having an epoxy group and a compound having two or more hydroxy groups and functioning as a crosslinking agent to react with each other. Alternatively, the above linking group can be formed by allowing a siloxane compound having a hydroxy group and a compound having two or more epoxy groups and functioning as a crosslinking agent to react with each other.

$*-CH(OH)CH_2S-*$

The linking group $*-CH(OH)CH_2S-*$ can be formed by, for example, allowing a siloxane compound having an epoxy group and a siloxane compound having a thiol group to react with each other.

Alternatively, the above linking group can be formed by allowing a siloxane compound having an epoxy group and a compound having two or more thiol groups and functioning as a crosslinking agent to react with each other. Alternatively, the above linking group can be formed by allowing a siloxane compound having a thiol group and a compound having two or more epoxy groups and functioning as a crosslinking agent to react with each other.

$*-CH(OH)CH_2NR^c-*$

The linking group $*-CH(OH)CH_2NR^c-*$ can be formed by, for example, allowing a siloxane compound having an epoxy group and a siloxane compound having an amino group to react with each other.

Alternatively, the above linking group can be formed by allowing a siloxane compound having an epoxy group and a compound having two or more amino groups and functioning as a crosslinking agent to react with each other. Alternatively, the above linking group can be formed by allowing a siloxane compound having an amino group and a compound having two or more epoxy groups and functioning as a crosslinking agent to react with each other.

$*-CH(CH_2OH)CH_2OCO-*$

The linking group $*-CH(CH_2OH)CH_2OCO-*$ can be formed by changing the epoxy group in the formation of the linking group $*-CH(OH)CH_2OCO-*$ to an oxetanyl group.

$*-CH(CH_2OH)CH_2O-*$

The linking group $*-CH(CH_2OH)CH_2O-*$ can be formed by changing the epoxy group in the formation of the linking group $*-CH(OH)CH_2O-*$ to an oxetanyl group.

$*-CH(CH_2OH)CH_2S-*$

The linking group $*-CH(CH_2OH)CH_2S-*$ can be formed by changing the epoxy group in the formation of the linking group $*-CH(OH)CH_2S-*$ to an oxetanyl group.

$*-CH(CH_2OH)CH_2NR^c-*$

The linking group $*-CH(CH_2OH)CH_2NR^c-*$ can be formed by changing the epoxy group in the formation of the linking group $*-CH(OH)CH_2NR^c-*$ to an oxetanyl group.

$*-CH_2CH_2-*$

The linking group $*-CH_2CH_2-*$ can be formed by, for example, a polymerization reaction of siloxane compounds having a vinyl group (such as a (meth)acryloyl group).

In the present invention, the linking structure through $*-CH_2CH_2-*$ does not include the linking structure through $*-S-CH_2CH_2-*$.

The siloxane compound layer may have one of the above linking structures or two or more of the above linking structures.

In the siloxane compound layer in the present invention, from the viewpoint of reactivity for forming the linking structure and chemical stability of the linking structure, the linking structure of siloxane compounds is preferably at least one linking structure through a linking group selected from $*-O-M-O-*$, $*-S-M-S-*$, $*-O-CH_2-O-*$, $*-S-CH_2CH_2-*$, $*-OC(=O)O-*$, $*-CH_2CH_2-*$, and $*-C(=O)O^-N^+(R^d)_3-*$ described above, more preferably at least one linking structure through a linking group selected from $*-O-M-O-*$, $*-S-M-S-*$, $*-O-CH_2-O-*$, $*-S-CH_2CH_2-*$, and $*-CH_2CH_2-*$, and still more preferably at least one linking structure through a linking group selected from $*-O-M-O-*$ and $*-CH_2CH_2-*$. Even still more preferably, the siloxane compound layer includes both the linking structure through $*-O-M-O-*$ and the linking structure through $*-CH_2CH_2-*$.

The siloxane compounds (siloxane compounds before the formation of the linking structure through the linking group) used as raw materials of the siloxane compound layer are not particularly limited as long as the siloxane compounds have functional groups that provide the above linking structure. Specific preferred examples of the polysiloxane compounds include at least one selected from methacrylate-modified polydialkylsiloxanes, methacrylate-modified polydiarylsiloxanes, methacrylate-modified polyalkylarylsiloxanes, thiol-modified polydialkylsiloxanes, thiol-modified polydiarylsiloxanes, thiol-modified polyalkylarylsiloxanes, hydroxy-modified polydialkylsiloxanes, hydroxy-modified polydiarylsiloxanes, hydroxy-modified polyalkylarylsiloxanes, amine-modified polydialkylsiloxanes, amine-modified polydiarylsiloxanes, amine-modified polyalkylarylsiloxanes, vinyl-modified polydialkylsiloxanes, vinyl-modified polydiarylsiloxanes, vinyl-modified polyalkylarylsiloxanes, carboxy-modified polydialkylsiloxanes, carboxy-modified polydiarylsiloxanes, carboxy-modified polyalkylarylsiloxanes, hydrosilyl-modified polydialkylsiloxanes, hydrosilyl-modified polydiarylsiloxanes, hydrosilyl-modified polyalkylarylsiloxanes, epoxy-modified polydialkylsiloxanes, epoxy-modified polydiarylsiloxanes, epoxy-modified polyalkylarylsiloxanes, oxetanyl-modified polydialkylsiloxanes, oxetanyl-modified polydiarylsiloxanes, and oxetanyl-modified polyalkylarylsiloxanes.

In the above polysiloxane compounds cited as examples, the site modified with each functional group may be a terminal or a side chain. The polysiloxane compounds preferably have two or more modified sites per molecule. Each of the functional groups introduced by the modification may further have a substituent.

The quantitative ratio of the alkyl group to the aryl group in each of the "polyalkylarylsiloxanes" is not particularly limited. Specifically, each of the "polyalkylarylsiloxanes" may have a dialkylsiloxane structure or a diarylsiloxane structure in the structure thereof.

In the siloxane compounds cited as examples, the number of carbon atoms of the alkyl group is preferably 1 to 10, more preferably 1 to 5, and still more preferably 1 to 3. The alkyl group is even still more preferably methyl. In the siloxane compounds cited as examples, the number of carbon atoms of the aryl group is preferably 6 to 20, more preferably 6 to 15, and still more preferably 6 to 12. The aryl group is even still more preferably phenyl.

The siloxane compound layer in the present invention preferably has at least one structure represented by (a) or (b). (a) A structure having a structure represented by General formula (1) and a structure represented by General formula (2) or General formula (3)

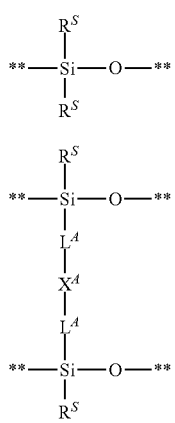

General formula (1)

General formula (2)

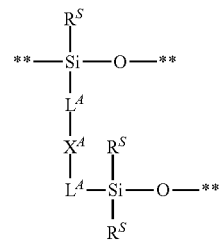

General formula (3)

(b) A structure represented by General formula (4)

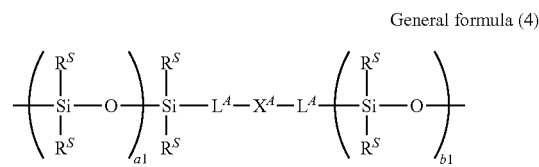

General formula (4)

In the formulae, $R^S$ represents an alkyl group or an aryl group; $L^A$ represents a single bond or a divalent linking group; $X^A$ represents a linking group selected from *—O—$M^1$—O—*, *—S—$M^1$—S—*, *—O—$CH_2$—O—*, *—S—$CH_2CH_2$—*, *—OC(=O)O—*, *—$CH_2CH_2$—*, and *—C(=O)O$^-$N$^+$(R$^d$)$_3$—* where $M^1$ represents Zr, Fe, Zn, B, Al, Ti, In or Ga and $R^d$ represents a hydrogen atom or an alkyl group; and a1 and b1 are each an integer of 2 or more (preferably an integer of 5 or more). The symbol "*" represents a linking site. The symbol "" represents a linking site in a siloxane bond (that is, in General formulae (1) to (3), when an O atom is adjacent to the symbol , the symbol  represents a site linking to a Si atom. In General formulae (1) to (3), when a Si atom is adjacent to the symbol , the symbol ** represents a site linking to an O atom.)

The terminal structure of General formula (4) is preferably a group selected from a hydrogen atom, a mercapto group, an amino group, a vinyl group, a carboxy group, an oxetane group, a sulfonic acid group, and a phosphonic acid group.

When $R^S$ and $R^d$ are each an alkyl group, the alkyl group is preferably an alkyl group having 1 to 10 carbon atoms, more preferably an alkyl group having 1 to 5 carbon atoms, still more preferably an alkyl group having 1 to 3 carbon atoms, and particularly preferably methyl.

When $R^S$ is an aryl group, the number of carbon atoms of the aryl group is preferably 6 to 20, more preferably 6 to 15, and still more preferably 6 to 12. The aryl group is even still more preferably a phenyl group.

When $L^A$ is a divalent linking group, the divalent linking group is preferably an alkylene group (preferably an alkylene group having 1 to 10 carbon atoms and more preferably an alkylene group having 1 to 5 carbon atoms), an arylene group (preferably an arylene group having 6 to 20 carbon atoms, more preferably an arylene group having 6 to 15 carbon atoms, and still more preferably a phenylene group), or —Si(R$^S$)$_2$—O— (where $R^S$ has the same definition as $R^S$ in General formula (2), and the preferred form of $R^S$ is also the same as that of $R^S$ in General formula (2)). The "O" in —Si(R$^S$)$_2$—O— is linked to Si in the above general formulae.

The structure of (a) above preferably has a repeating unit represented by Formula (5) besides the structure represented by any of General formulae (1) to (3).

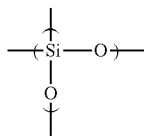

Formula (5)

It is also preferable that the repeating unit represented by Formula (5) be present in the siloxane compound layer in the form of a structure in which the repeating units represented by Formula (5) are linked to each other through a siloxane bond.

In the siloxane compound layer in the present invention, a content ratio of the repeating unit represented by Formula (5) is preferably 0.01 to 0.55, more preferably 0.03 to 0.40, still more preferably 0.05 to 0.25, and particularly preferably 0.10 to 0.20.

The content ratio of the repeating unit represented by Formula (5) is measured by the method described in Examples below.

In the present invention, the thickness of the siloxane compound layer is preferably 10 to 3,000 nm, and more preferably 100 to 1,500 nm.

Gas Separation Membrane

Composite Gas Separation Membrane

In a composite gas separation membrane which is a preferred embodiment of a gas separation membrane of the present invention (hereinafter, may be referred to as "composite membrane of the present invention"), a gas separation layer containing the poly(benzoxazole-imide) compound described above is formed on the upper side of a gas-permeable support layer (porous layer). As described later, this composite membrane can be formed by applying (the term "applying" (or "coating") used herein includes a manner of deposition on a surface by immersion), to at least a surface of a porous support, a coating solution (dope) containing a precursor (polyimide compound) of a component that forms the gas separation layer. Furthermore, in the composite membrane of the present invention, the siloxane compound layer described above is preferably formed on the upper side of the gas separation layer so as to be in contact with the gas separation layer.

FIG. 1 is a schematic sectional view illustrating a composite gas separation membrane 10 according to a preferred embodiment of the present invention. Reference numeral 1 indicates a gas separation layer, and reference numeral 2 indicates a porous layer.

Figure 2:
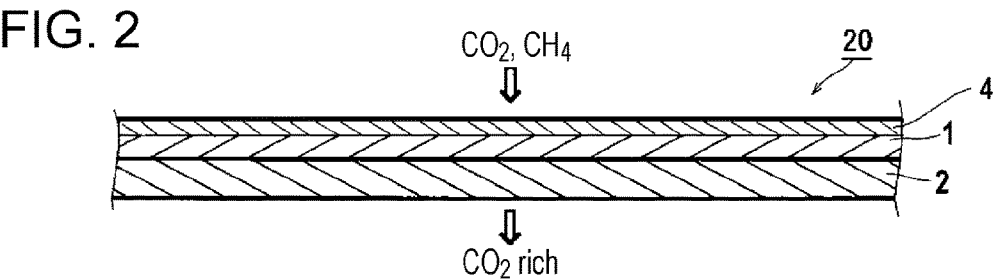
FIG. 2 is a schematic sectional view illustrating a gas separation membrane according to another embodiment (composite membrane) of the present invention.

FIG. 2 is a schematic vertical sectional view illustrating a composite gas separation membrane 20 according to another preferred embodiment of the present invention. Reference numeral 1 indicates a gas separation layer, reference numeral 2 indicates a porous layer, and reference numeral 4 indicates a siloxane compound layer.

Figure 3:
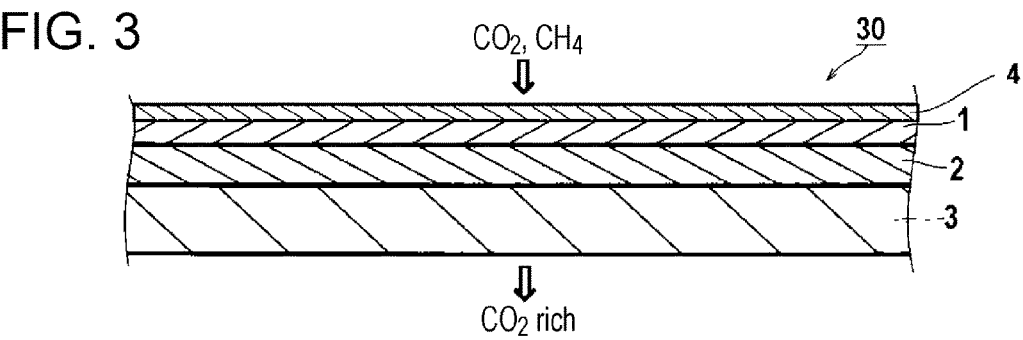
FIG. 3 is a schematic sectional view illustrating a gas separation membrane according to still another embodiment (composite membrane) of the present invention.

FIG. 3 is a schematic sectional view illustrating a composite gas separation membrane 30 according to still another preferred embodiment of the present invention. In this embodiment, in addition to the gas separation layer 1, the porous layer 2, and the siloxane compound layer 4, a nonwoven fabric layer 3 is provided as an additional support layer.

Figure 4:
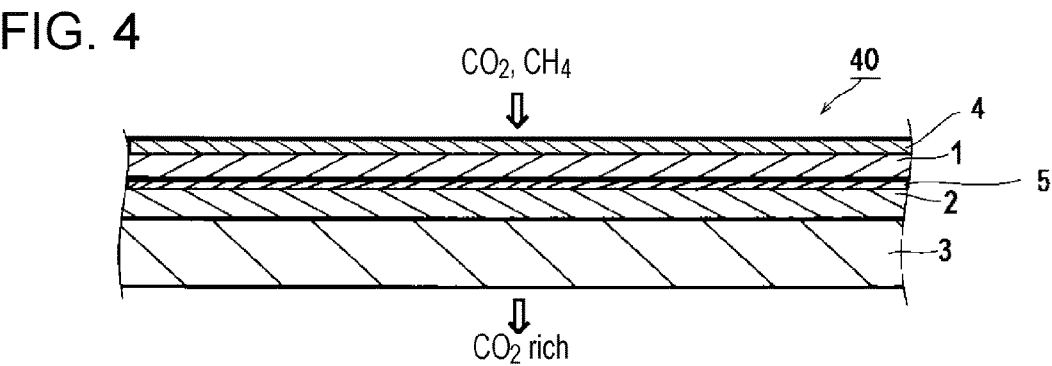
FIG. 4 is a schematic sectional view illustrating a gas separation membrane according to still another embodiment (composite membrane) of the present invention.

FIG. 4 is a schematic sectional view illustrating a composite gas separation membrane 40 according to still another preferred embodiment of the present invention. In this embodiment, in addition to the gas separation layer 1, the porous layer 2, the siloxane compound layer 4, and the nonwoven fabric layer 3, a smooth layer 5 is provided as an underlayer of the gas separation layer 1 so as to be in contact with the gas separation layer 1.

Herein, the term "on the upper side of a support layer" means that another layer may be disposed between a support layer and a gas separation layer. Regarding the expression of the upper and lower sides, the side to which target gas to be separated is supplied is defined as the "upper side", and the side from which the separated gas is discharged is defined as the "lower side" unless otherwise stated.

Herein, the term "having gas permeability" means that when carbon dioxide is supplied at a total pressure on the gas supply side of 4 MPa at a temperature of 40° C., the permeation rate of the carbon dioxide is $1 \times 10^{-5}$ cm$^3$ (STP)/ cm$^2$·sec·cmHg (10 GPU) or more. The gas permeability is preferably 20 GPU or more, more preferably 50 GPU or more, and still more preferably 100 GPU or more. The term "gas separation capability" refers to a membrane performance in which when mixed gas containing two or more types of gas is supplied, the permeance of particular gas becomes higher than the permeance of another gas. A ratio $R_{CO2}/R_{CH4}$ described later is preferably 20 or more. The "gas separation layer" in the present invention is a layer having the gas separation capability.

In the composite membrane of the present invention, a gas separation layer may be formed and disposed on a surface or in an inner surface of a porous layer. A composite membrane can be easily obtained by forming a gas separation layer at least on a surface of a porous layer. Formation of a gas separation layer at least on a surface of a porous layer can provide a composite membrane having an advantage that high separation selectivity, high gas permeability, and mechanical strength are combined. The thickness of the separation layer is preferably as small as possible under conditions in which high gas permeability is provided while mechanical strength and separation selectivity are maintained.

In the composite membrane of the present invention, the thickness of the gas separation layer is not particularly limited, but is preferably 0.01 to 5.0 μm, more preferably 0.05 to 2.0 μM, and still more preferably 0.05 to 1.0 μm.

The porous layer is not particularly limited as long as the purpose of providing mechanical strength and high gas permeability is satisfied. The porous layer may be formed of an organic material or an inorganic material. The porous layer is preferably a porous membrane formed of an organic polymer. The thickness of the porous layer is 1 to 3,000 μm, preferably 5 to 500 μm, and more preferably 5 to 150 Regarding the pore structure of the porous layer, the average pore size is usually 10 μm or less, preferably 0.5 μm or less, and more preferably 0.2 μm or less. The porosity is preferably 20% to 90%, and more preferably 30% to 80%.

The porous layer preferably has a molecular weight cut-off of 100,000 or less. Furthermore, the gas permeance of the porous layer is preferably $3 \times 10^{-5}$ cm$^3$ (STP)/ cm$^2$·sec·cmHg (30 GPU) or more, more preferably 100 GPU or more, and still more preferably 200 GPU or more in terms of the permeation rate of carbon dioxide at 40° C. and 4 MPa.

Examples of the material of the porous layer include known polymers such as polyolefin resins, e.g., polyethylene and polypropylene; fluorine-containing resins, e.g., polytetrafluoroethylene, polyvinyl fluoride, and polyvinylidene fluoride; and other resins, e.g., polystyrene, cellulose acetate, polyurethane, polyacrylonitrile, polyphenylene oxide, polysulfone, polyethersulfone, polyimide, and polyaramid.

The porous layer may have any shape such as a flat-plate shape, a spiral shape, a tubular shape, or a hollow fiber shape.

The composite membrane of the present invention preferably has a support for providing mechanical strength, the support being disposed on the lower side of the porous layer that forms a gas separation layer. Examples of the support include woven fabrics, nonwoven fabrics, and nets. From the viewpoint of membrane formability and the cost, a nonwoven fabric is suitably used. As the nonwoven fabric, fibers formed of polyester, polypropylene, polyacrylonitrile, polyethylene, polyamide, or the like may be used alone or in combination of two or more thereof. The nonwoven fabric can be produced by, for example, papermaking main fibers and binder fibers that are uniformly dispersed in water with a circular net, a long net, or the like, and drying the fibers with a dryer. Furthermore, for the purpose of, for example, removing fuzz or improving mechanical properties, it is also preferable to perform a thermal pressing process by interposing the nonwoven fabric between two rolls.

In the production of a composite membrane of the present invention, the gas separation layer can be formed by applying a coating solution containing at least the polyimide compound described above to a porous layer or a smooth layer, which will be described later, drying the coating solution, and subsequently performing heat treatment at about 300° C. to 600° C. to convert the polyimide compound to a poly(benzoxazole-imide) compound. The time of the heat treatment is usually 0.5 to 3 hours, though it depends on the temperature.

The content of the polyimide compound in the coating solution is not particularly limited, but is preferably 0.1% to 30% by mass, and more preferably 0.5% to 10% by mass. When the content of the polyimide compound is excessively low, the coating solution easily permeates through the lower layer (porous support) in the application of the coating solution onto the porous layer. Accordingly, there is a concern that defects are likely to be generated in a surface layer that contributes to separation. When the content of the polyimide compound is excessively high, in the formation of a membrane on a porous layer, pores are filled with the polyimide compound at a high concentration, which may decrease gas permeability.

As the organic solvent serving as a medium of the coating solution for forming the gas separation layer, it is preferable to select a suitable organic solvent that does not erode a support to which the coating solution is to be applied. Examples of the organic solvent include hydrocarbon organic solvents such as n-hexane and n-heptane; ester organic solvents such as methyl acetate, ethyl acetate, and butyl acetate; lower alcohols such as methanol, ethanol, n-propanol, isopropanol, n-butanol, isobutanol, and tert-butanol; aliphatic ketones such as acetone, methyl ethyl ketone, methyl isobutyl ketone, diacetone alcohol, cyclopentanone, and cyclohexanone; polyhydric alcohol such as ethylene glycol, diethylene glycol, triethylene glycol, glycerin, and propylene glycol; ether organic solvent such as ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, dibutyl ether, tetrahydrofuran, methyl cyclopentyl ether, and dioxane; N-methylpyrrolidone; 2-pyrrolidone; dimethylformamide; dimethylimidazolidinone; dimethyl sulfoxide; and dimethylacetamide. These organic solvents are suitably selected within a range that does not adversely affect the support through erosion or the like. Esters (preferably, butyl acetate), alcohols (preferably, methanol, ethanol, isopropanol, and isobutanol), aliphatic ketones (preferably, methyl ethyl ketone, methyl isobutyl ketone, diacetone alcohol, cyclopentanone, and cyclohexanone), and ethers (ethylene glycol, diethylene glycol monomethyl ether, and methyl cyclopentyl ether) are preferable. Aliphatic ketones, alcohols, and ethers are more preferable. These organic solvents may be used alone or in combination of two or more thereof.

In the composite membrane of the present invention, the siloxane compound layer described above is preferably disposed on the upper side of the gas separation layer so as to be in contact with the gas separation layer. The siloxane compound layer can be preferably formed by applying, onto the gas separation layer, a coating solution containing at least a siloxane compound (at least one siloxane compound having a reactive group for forming any of the linking groups described above), performing light irradiation, heat treatment, or the like optionally in the presence of a catalyst, a condensing agent, and a polymerization initiator to link siloxane compounds through a desired linking group.

The content of the siloxane compound in the coating solution is not particularly limited, but is preferably 0.1% to 30% by mass, and more preferably 0.5% to 10% by mass.

A medium of the coating solution for forming the siloxane compound layer is preferably a solvent selected from pentane, hexane, heptane, octane, nonane, decane, benzene, toluene, xylene, N-methylpyrrolidone, N-ethylpyrrolidone, dimethyl sulfoxide, dimethylacetamide, dimethylformamide, methylene chloride, dioxane, and 1,3-dioxolane.

In the composite membrane of the present invention, the thickness of the siloxane compound layer is preferably 0.01 to 5 μm, and more preferably 0.05 to 1 μm from the viewpoint of smoothness and gas permeability.

The gas permeance of the siloxane compound layer at 40° C. and 4 MPa is preferably 100 GPU or more, more preferably 300 GPU or more, and still more preferably 1,000 GPU or more in terms of the permeation rate of carbon dioxide.

Another Layer

In the composite membrane of the present invention, it is also preferable to provide a smooth layer as an underlayer in contact with the gas separation layer, the smooth layer being disposed between the porous layer and the gas separation layer. When the smooth layer is provided, it is possible to smooth the unevenness on the surface of the porous layer and thus a reduction in the thickness of the gas separation layer is easily realized. This smooth layer is preferably a siloxane compound layer. The preferred form of the siloxane compound layer is the same as that of the siloxane compound layer described above.

Asymmetric Gas Separation Membrane

Figure 5:
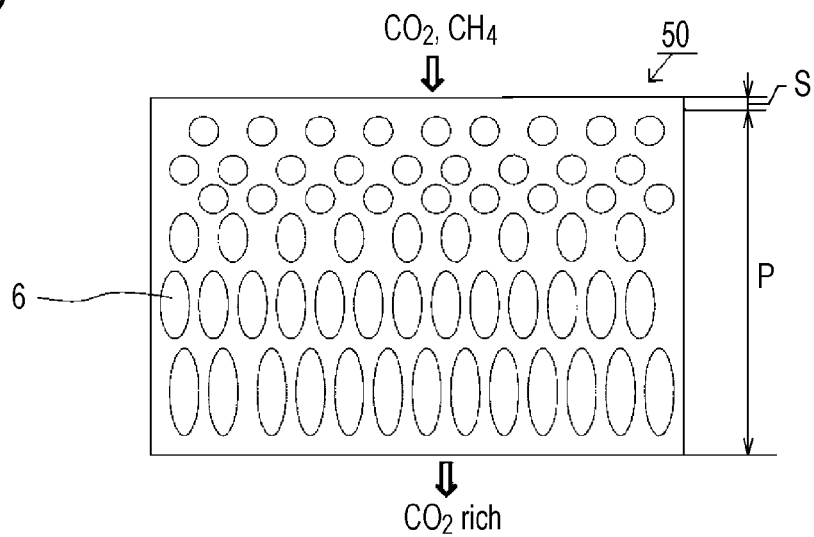
FIG. 5 is a schematic view illustrating a gas separation membrane according to still another embodiment (asymmetric membrane) of the present invention.

It is also preferable that the gas separation membrane of the present invention have a form of an asymmetric membrane. FIG. 5 is a schematic view illustrating a preferred embodiment of an asymmetric gas separation membrane of the present invention. In an asymmetric gas separation membrane 50, a thin dense layer S (hereinafter, may be referred to as "skin layer" or "gas separation layer") that contributes to gas separation is formed on the gas supply side. A portion other than the dense layer is a thick porous layer P having pores 6. This porous layer functions as a support. The pores in the porous layer P penetrate from an end on the upper side (surface in contact with the dense layer S) to an end on the lower side, and, unlike the dense layer S, the porous layer P does not have a gas separation capability.

Figure 6:
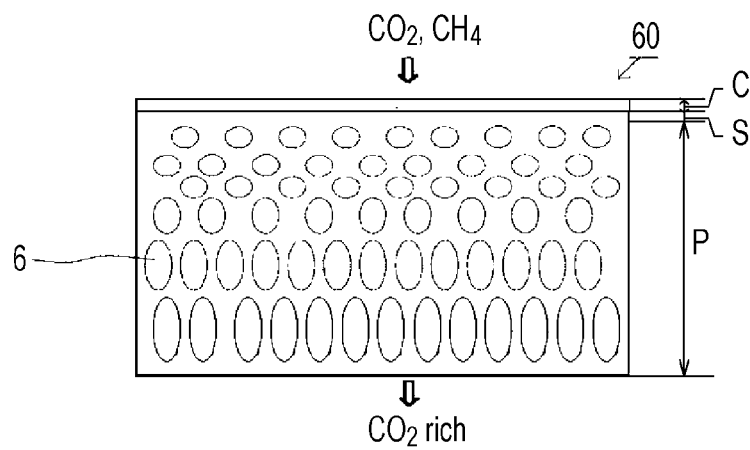
FIG. 6 is a schematic view illustrating a gas separation membrane according to still another embodiment (asymmetric membrane) of the present invention.

It is also preferable that, as illustrated in FIG. 6, the asymmetric gas separation membrane of the present invention have a siloxane compound layer C (hereinafter, may be referred to as "protective layer") that is the same as the siloxane compound layer described above and disposed on the dense layer (i.e., gas separation layer).

The asymmetric gas separation membrane of the present invention can be formed by forming an asymmetric membrane by a phase inversion process using a solution (dope solution) containing the polyimide compound described above, and heat-treating the asymmetric membrane at about 300° C. to 600° C. to convert the polyimide compound to a poly(benzoxazole-imide) compound. The time of the heat treatment is usually 0.5 to 3 hours, though it depends on the temperature.

The phase inversion process is a known process for forming a membrane by bringing a dope solution into contact with a coagulating liquid while causing a phase inversion, and a so-called dry-wet process is suitably used in the present invention. The dry-wet process includes evaporating a solution on a surface of a dope solution that is formed to have a membrane shape, and subsequently immersing the resulting membrane in a coagulating liquid (a solvent which is compatible with a solvent of the dope solution and in which the polyimide compound in the dope solution is insoluble) to form a dense layer and to simultaneously form a porous layer by forming fine pores using a phase-separation phenomenon that occurs at this time. This process was suggested by Loeb, Sourirajan, et al. (for example, the specification of U.S. Pat. No. 3,133,132).

Through the step of evaporating the solution on the surface of the dope solution, the solvent is volatilized from the surface of the coating solution, and moisture in the air is absorbed. As a result, the surface becomes solidified easily, and it is possible to stabilize the thickness of the dense layer (skin layer) formed when the resulting membrane is brought into contact with the coagulating liquid.

A medium used in the preparation of the dope solution is preferably a solvent miscible with the coagulating liquid so as to cause phase inversion. More preferably, as the medium of the dope solution, an aprotic polar organic solvent selected from N-methylpyrrolidone, N-ethylpyrrolidone, γ-butyrolactone, dimethyl sulfoxide, dimethylacetamide, dimethylformamide, methylene chloride, tetrahydrofuran, dioxane, and 1,3-dioxolane is at least used. It is also preferable that a solvent such as a ketone, an alcohol, acetonitrile, or water be further mixed with any of the solvents mentioned above to prepare the medium of the dope solution.

The coagulating liquid is preferably formed of a mixture of water and a protic polar solvent (preferably, an alcohol).

The dope solution can be applied onto a porous support. Examples of the support include gas-permeable porous membranes such as nanofiltration membranes, ultrafiltration membranes, microfiltration membranes, woven fabrics, and nonwoven fabrics. Of these, nonwoven fabrics are preferable. As the nonwoven fabric, fibers formed of polyester, polypropylene, polyacrylonitrile, polyethylene, polyamide, or the like may be used alone or in combination of two or more thereof. The nonwoven fabric can be produced by, for example, papermaking main fibers and binder fibers that are uniformly dispersed in water with a circular net, a long net, or the like, and drying the fibers with a dryer. Furthermore, for the purpose of, for example, removing fuzz or improving mechanical properties, it is also preferable to perform a thermal pressing process by interposing the nonwoven fabric between two rolls.

When a dope solution is applied onto a porous membrane such as a nonwoven fabric, part of the dope solution permeates through pores of the porous membrane, and a phase-separation phenomenon occurs in this state. Therefore, the resulting asymmetric membrane may be integrated with the porous membrane such as a nonwoven fabric to form a gas separation membrane. That is, it is also preferable that the porous layer include a porous support and fine pores formed by curing the dope solution. Herein, this state is denoted by the phase "an asymmetric membrane is supported by a porous membrane".

The thickness of the asymmetric membrane of the present invention is preferably 10 to 200 μm (when the asymmetric membrane is supported by a porous membrane such as a nonwoven fabric, the term "thickness" refers to a thickness including the thickness of the porous membrane). The thickness of the surface layer (i.e., gas separation layer) that is referred to as a dense layer or a skin layer and that contributes to gas separation is not particularly limited. However, from the viewpoint of providing practical gas permeability, the thickness of the surface layer is preferably 0.01 to 5.0 μm, more preferably 0.05 to 2.0 μm, and still more preferably 0.05 to 1.0 μm.

The asymmetric gas separation membrane of the present invention may be a flat membrane or a hollow-fiber membrane. Asymmetric hollow-fiber membranes can be produced by a dry-wet spinning process. The dry-wet spinning process is a process for producing an asymmetric hollow-fiber membrane by applying a dry-wet process to a dope solution which is ejected from a spinning nozzle to have a desired hollow fiber shape. More specifically, the dry-wet spinning process is a process for producing an asymmetric membrane by ejecting a dope solution from a nozzle to have a desired hollow fiber shape, allowing the dope solution to pass through air or a nitrogen gas atmosphere immediately after the ejection, and then immersing the resulting dope solution in a coagulating liquid which does not substantially dissolve a polyimide compound and which is compatible with a solvent of the dope solution to form an asymmetric structure, then drying the dope solution, and further performing heat treatment as needed.

The solution viscosity of the dope solution to be ejected from a nozzle is 2 to 1,700 Pa·s, preferably 10 to 1,500 Pa·s, and particularly preferably 20 to 1,000 Pa·s at an ejection temperature (for example, 10° C.) because the shape after ejection, such as a hollow fiber shape, can be stably obtained. It is preferable that immersion in a coagulating liquid be performed by immersing the ejected dope solution in a primary coagulating liquid to be coagulated to such an extent that the shape of the membrane such as a hollow fiber can be maintained, then winding the resulting membrane around a guide roll, and subsequently immersing the membrane in a secondary coagulating liquid so as to sufficiently coagulate the whole membrane. It is effective that the coagulated membrane is dried after the coagulating liquid is substituted with a solvent such as a hydrocarbon.

In the gas separation membrane of the present invention, the content of the poly(benzoxazole-imide) compound in the gas separation layer is not particularly limited as long as a desired gas separation performance is obtained. From the viewpoint of improving the gas separation performance, the content of the poly(benzoxazole-imide) compound in the gas separation layer is preferably 20% by mass or more, more preferably 40% by mass or more, and still more preferably 50% by mass or more. The content of the poly(benzoxazole-imide) compound in the gas separation layer may be 100% by mass but is usually 99% by mass or less.

The gas separation layer formed as described above may be cured as required. In the present invention, when the polyimide compound used in the formation of a gas separation layer has a group that generates a radical and is capable of forming a crosslinked structure, for example, —C(=O)— or —SO$_2$—, a crosslinked structure can be introduced in the polymer by ultraviolet (UV) irradiation, heat treatment, or the like to cure the gas separation layer.

In the gas separation membrane of the present invention, it is also preferable that the gas separation layer contain polymers other than the poly(benzoxazole-imide) compound (hereinafter, referred to as "other polymers") in addition to the poly(benzoxazole-imide) compound. Examples of the other polymers include at least one polymer selected from polyacrylonitrile compounds, polystyrene compounds, polyethersulfone compounds, polytetrafluoroethylene compounds, cellulose acetate compounds, polyether ether ketone compounds, polyamide compounds, polysulfone compounds, sulfonated polysulfone compounds, sulfonated polyethersulfone compounds, and polyvinylpyrrolidone compounds. When the gas separation layer contains other polymers, from the viewpoint of improving membrane formability (yield) of the gas separation membrane, the gas separation layer preferably contains the poly(benzoxazole-imide) compound and at least one selected from polystyrene compounds and polyethersulfone compounds.

When the gas separation layer contains other polymers, the content of the other polymers in the total amount of the poly(benzoxazole-imide) compound and the other polymers is preferably 5% to 50% by mass, and more preferably 10% to 40% by mass.

Use and Characteristics of Gas Separation Membrane

The gas separation membranes (composite membranes and asymmetric membranes) of the present invention can be suitably used for gas separation-recovery and gas separation-purification. For example, it is possible to obtain gas separation membranes that are capable of efficiently separating specific gas from a gas mixture containing gas such as hydrogen, helium, carbon monoxide, carbon dioxide, hydrogen sulfide, oxygen, nitrogen, ammonia, sulfur oxides, nitrogen oxides, hydrocarbons, e.g., methane and ethane, unsaturated hydrocarbons, e.g., propylene, and perfluoro compounds, e.g., tetrafluoroethane. In particular, it is preferable to obtain a gas separation membrane that selectively separates carbon dioxide from a gas mixture containing carbon dioxide and a hydrocarbon (methane).

When the gas to be subjected to a separation treatment is mixed gas of carbon dioxide and methane, the permeation rate of carbon dioxide at 40° C. and 5 MPa is preferably more than 20 GPU, more preferably more than 30 GPU, and still more preferably 50 to 500 GPU. The ratio of the permeation rate of carbon dioxide to the permeation rate of methane ($R_{CO2}/R_{CH4}$, may be referred to as "separation selectivity") is preferably 15 or more, more preferably 20 or more, still more preferably 23 or more, and particularly preferably 25 to 50 where $R_{CO2}$ represents the permeation rate of carbon dioxide and $R_{CH4}$ represents the permeation rate of methane.

Note that 1 GPU is $1 \times 10^{-6}$ cm$^3$ (STP)/cm$^2$·sec·cmHg.

Other Components

In order to adjust liquid physical properties of the dope solution, for example, a nonionic surfactant, a cationic surfactant, or an organofluorine compound may be added to the gas separation membrane of the present invention.

Specific examples of the surfactants include anionic surfactants such as alkyl benzene sulfonates, alkyl naphthalene sulfonates, higher fatty acid salts, sulfonates of higher fatty acid esters, sulfuric acid ester salts of higher alcohol ethers, sulfonates of higher alcohol ethers, alkyl carboxylates of higher alkyl sulfonamides, and alkyl phosphates; nonionic surfactants such as polyoxyethylene alkyl ethers, polyoxyethylene alkyl phenyl ethers, polyoxyethylene fatty acid esters, sorbitan fatty acid esters, ethylene oxide adducts of acetylene glycol, ethylene oxide adducts of glycerin, and polyoxyethylene sorbitan fatty acid esters; amphoteric surfactants such as alkyl betaines and amide betaines; silicon-based surfactants; and fluorine-based surfactants. The surfactant can be suitably selected from known surfactants including the above specific examples and derivatives thereof.

A high-molecular-weight dispersant may also be contained. Specific examples of the high-molecular-weight dispersant include polyvinylpyrrolidone, polyvinyl alcohol, polyvinyl methyl ether, polyethylene oxide, polyethylene glycol, polypropylene glycol, and polyacrylamide. Of these, polyvinylpyrrolidone is preferably used.

The conditions for forming the gas separation membrane of the present invention are not particularly limited. The temperature is preferably −30° C. to 100° C., more preferably −10° C. to 80° C., and particularly preferably 5° C. to 50° C.

In the present invention, during the formation of the membrane, gas such as air or oxygen may be allowed to coexist. However, it is desirable that the membrane be formed under an inert gas atmosphere.

Method for Separating Gas Mixture

A gas separation method of the present invention is a method that includes selectively allowing permeation of specific gas from mixed gas containing two or more types of gas by using the gas separation membrane of the present invention to perform separation. In particular, the gas separation method of the present invention is preferably a method that includes selectively allowing permeation of carbon dioxide from mixed gas containing carbon dioxide and methane. The pressure of gas during the gas separation is preferably 0.5 to 10 MPa, more preferably 1 to 10 MPa, and still more preferably 2 to 7 MPa.

The temperature of gas when the gas separation method of the present invention is performed is preferably −30° C. to 90° C., and more preferably 15° C. to 70° C. In the mixed gas containing carbon dioxide and methane gas, the mixing ratio of carbon dioxide to methane gas is not particularly limited. The mixing ratio is preferably carbon dioxide:methane gas=1:99 to 99:1 (volume ratio) and more preferably carbon dioxide:methane gas=5:95 to 90:10 (volume ratio).

Gas Separation Module and Gas Separation Apparatus

A gas separation module can be prepared by using the gas separation membrane of the present invention. Examples of the module include a spiral-type module, a hollow fiber-type module, a pleated module, a tubular module, and a plate & frame-type module.

Furthermore, a gas separation apparatus having means for performing separation and recovery of gas or performing separation and purification of gas can be obtained by using the gas separation membrane or the gas separation module of the present invention. The gas separation membrane of the present invention may be applied to a gas separation-recovery apparatus for a membrane/absorption hybrid method in which a membrane is used in combination with an absorption liquid, as described in, for example, Japanese Unexamined Patent Application Publication No. 2007-297605.

EXAMPLES

The present invention will be described in more detail with reference to Examples. The present invention is not limited to these Examples.

Synthesis Examples

Synthesis of Polyimide PI-01

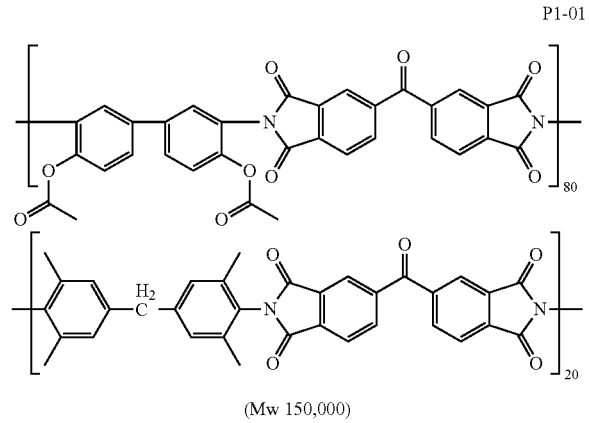

(Mw 150,000)

In a nitrogen atmosphere, 3,3',5,5'-tetramethyl-4,4'-methylenedianiline (5.09 g) and 3,3'-dihydroxybenzidine (17.30 g) were added in a 1 L flask and dissolved in N-methylpyrrolidone (300 g) that was added thereto. The resulting solution was cooled to −10° C., and 3,3',4,4'-benzophenonetetracarboxylic dianhydride (32.22 g) was then added thereto. The temperature of the reaction solution was raised to 30° C. in an oil bath, and stirring was then conducted for 24 hours. Pyridine (2.37 g) and acetic anhydride (30.63 g) were added to the reaction solution after stirring. The temperature of the reaction solution was raised to 80° C., and stirring was then conducted for five hours. The reaction solution was cooled to room temperature. The produced polymer was precipitated by using methanol and isolated as a solid. The polymer was further washed with methanol and dried under reduced pressure at 150° C. for 24 hours. As a result, a polyimide PI-01 was obtained. In Examples, the numerical values in each formula represent a molar ratio of structural units.

Synthesis of Polyimides PI-02 to PI-13

Polyimides PI-02 to PI-13 having the structural units (repeating units) shown below were synthesized in accordance with the synthesis example described above.

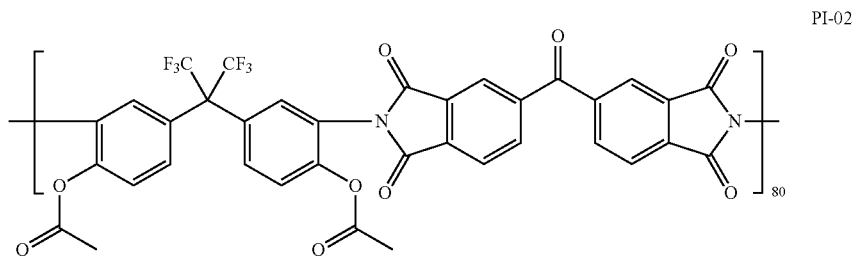

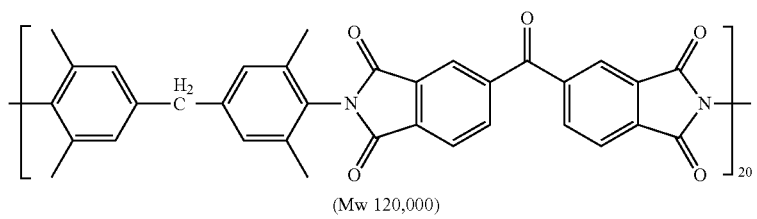

(Mw 120,000)

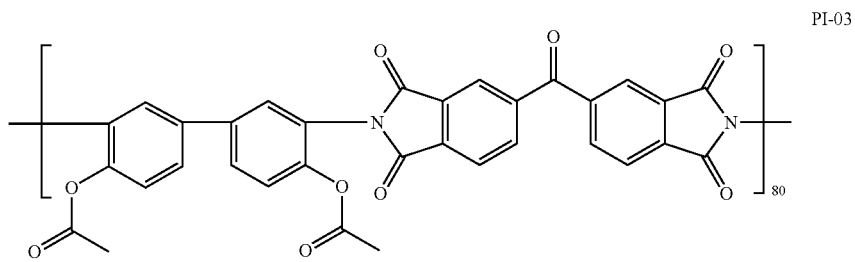

-continued
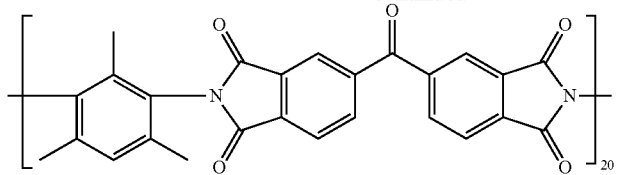
(Mw 135,000)
PI-04
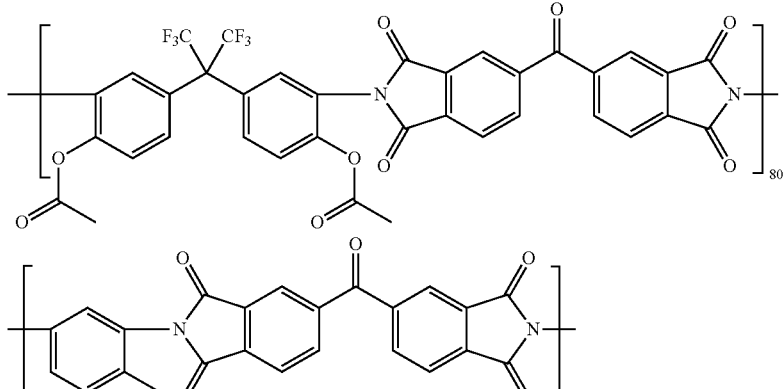
(Mw 160,000)
PI-05
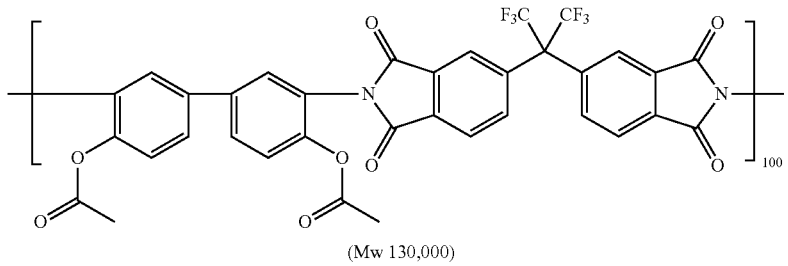
(Mw 130,000)
PI-06
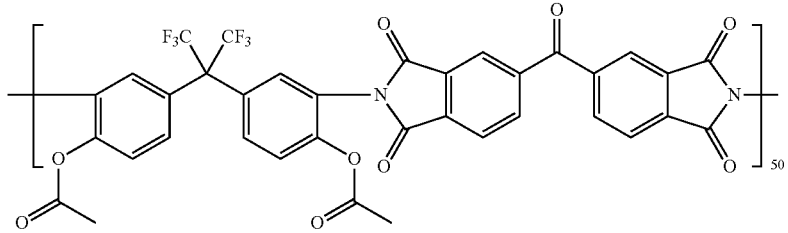
(Mw 110,000)

-continued
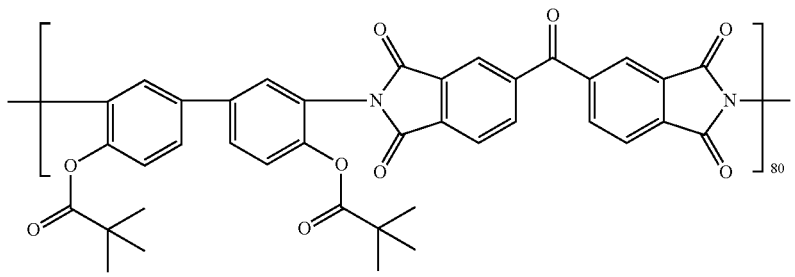
PI-07
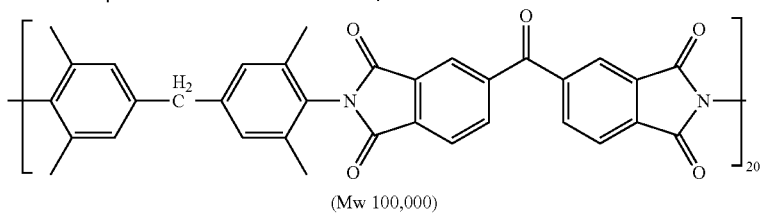
(Mw 100,000)
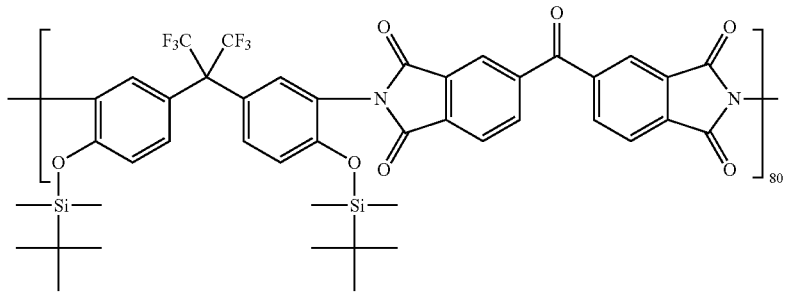
PI-08
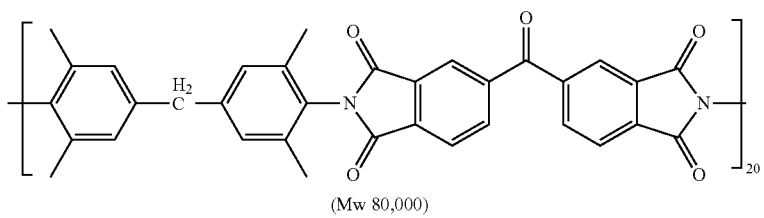
(Mw 80,000)
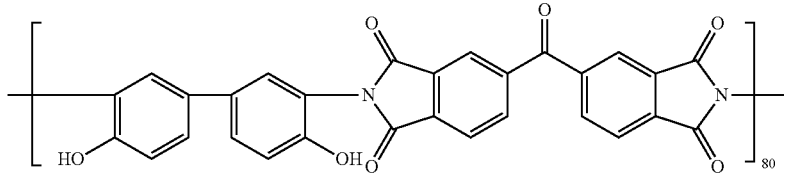
PI-09
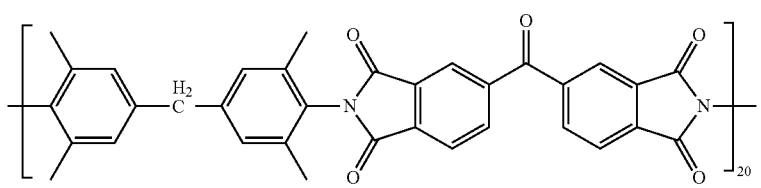
(Mw 300,000)
(PI-09 was synthesized as in the synthesis method of PI-01 except that 150 g of toluene was added instead of pyridine and acetic anhydride and the reaction solution was allowed to react at 180° C. for 12 hours.)

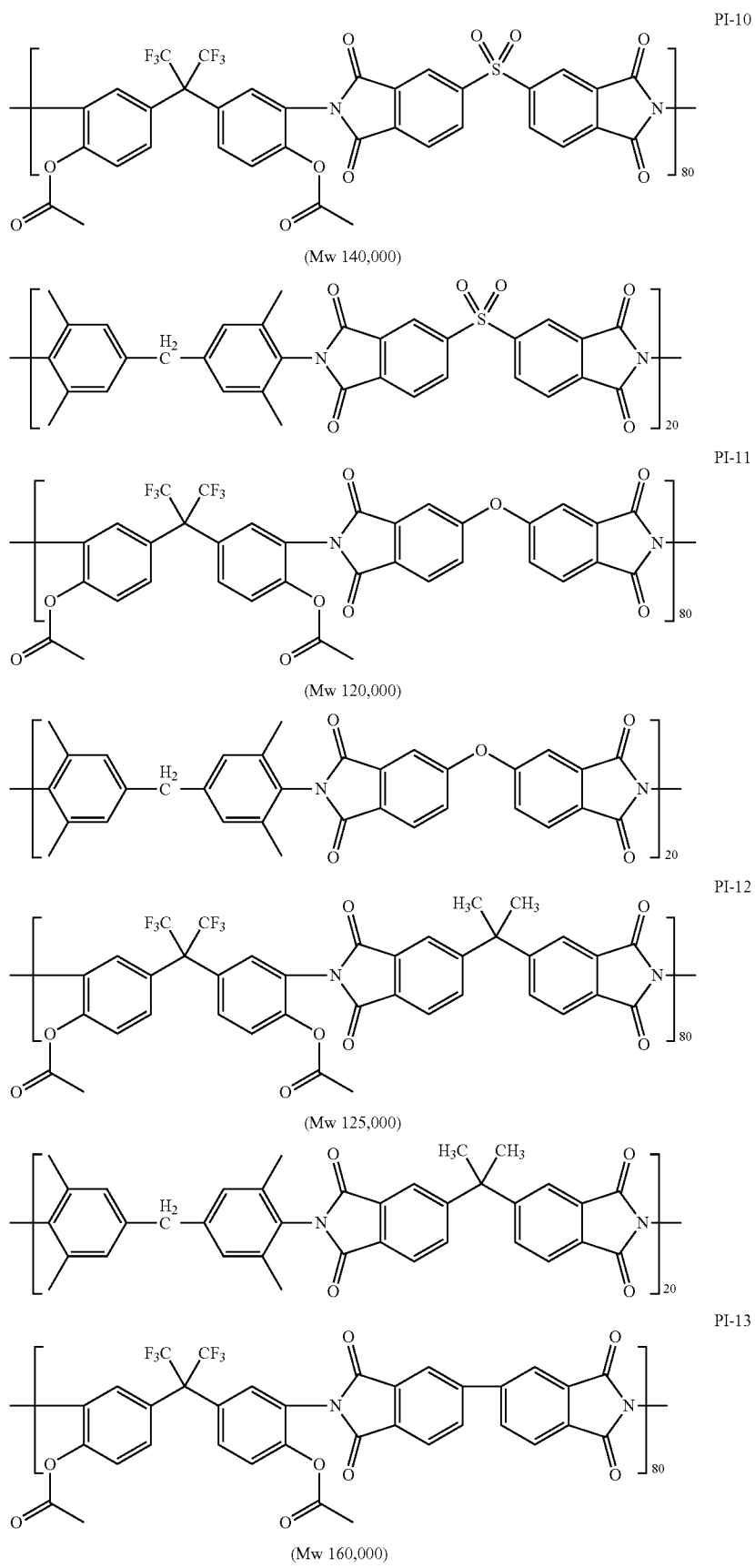

-continued

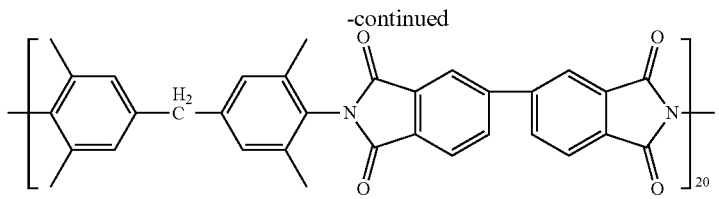

[Example 1] Preparation of Asymmetric Flat-Shaped Gas Separation Membrane

Preparation of Flat Membrane

The polyimide PI-01 (13.2 g), N-methylpyrrolidone (NMP) (23.5 g), 1,3-dioxolane (52.1 g), acetone (4.09 g), and methanol (2.79 g) were mixed, and the resulting mixture was degassed to prepare a dope solution. A polyester nonwoven fabric (available from Awa Paper Mfg. Co., Ltd., thickness: 95 μm) was placed on a clean glass plate (10 cm in length×10 cm in width×3 mm in thickness, hereinafter the same), and the dope solution was cast on the nonwoven fabric. The glass plate was then immersed in a water tank at 0° C. for five minutes to cause gelation of the dope solution. The temperature of water in the water tank was then raised to 88° C., and annealing was conducted for 10 minutes to obtain a polyimide membrane. Subsequently, the polyimide membrane was dried at 80° C. for five hours, and the resulting membrane was then heat-treated at 400° C. for one hour to thereby convert the polyimide PI-01 to PBO-PI-01 shown below. In this manner, a flat membrane with an asymmetric structure having a dense layer (gas separation layer) containing a poly(benzoxazole-imide) compound and having a thickness of 150 nm, a porous layer adjacent to the dense layer and having a thickness of 100 μm, and a nonwoven fabric layer was obtained. The molar ratio of structural units of PBO-PI-01 constituting the dense layer (gas separation layer) was calculated by XPS analysis in accordance with the method described in Journal of Membrane Science 2012, Vol. 397-398, pp. 51-65. The ratio m/(n+q) was 1.0.

Regarding flat membranes produced in Examples and Comparative Examples described below, the thickness of the dense layer and the thickness of the porous layer were respectively controlled to be substantially the same as those of the gas separation membrane of Example 1 (specifically, the difference between the thickness of the dense layer of each of the flat membranes and the thickness of the dense layer of Example 1 was controlled within the range of ±20 nm, and the difference between the thickness of the porous layer of each of the flat membranes and the thickness of the porous layer of Example 1 was controlled within the range of ±20 μm).

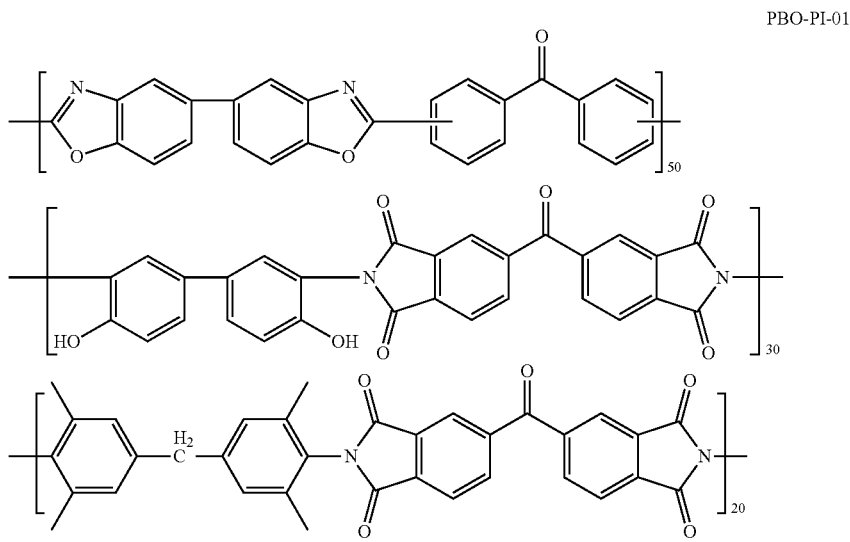

PBO-PI-01

Crosslinking Treatment of Gas Separation Layer

Subsequently, the flat membrane was irradiated with UV with an integrated illuminance of 1.5 $J/cm^2$ to cure the flat membrane.

Formation of Protective Layer

Vinyl Q resin (available from Gelest, Inc., product No. VQM-135) (10 g), hydrosilyl PDMS (available from Gelest, Inc., product No. HMS-301) (1 g), a Karstedt catalyst (available from Sigma-Aldrich Japan K.K., product No. 479527) (5 mg), and heptane (90 g) were mixed to prepare a composition (mixed liquid) for forming a siloxane compound layer. The mixed liquid was applied onto the dried dense layer (gas separation layer) by spin coating and cured by drying at 80° C. for five hours, thus obtaining a gas separation membrane (Example 1) which had a siloxane compound layer with a thickness of 500 nm (on which a protective layer is formed) on the gas separation layer. Hereinafter, a gas separation membrane obtained by using a flat membrane having an asymmetric structure may be referred to as "asymmetric flat-shaped gas separation membrane".

[Examples 2 to 5] Preparation of Asymmetric Flat-Shaped Gas Separation Membranes Gas separation membranes of Examples 2 to 5 were obtained as in Example 1 except that, in Example 1, the raw materials used in the preparation of the composition for forming a siloxane compound layer were changed as shown in a table below, and curing of the siloxane compound layer was conducted by ultraviolet (UV) irradiation in the presence of an additive shown in the table below. The formation of the siloxane compound layer in Example 2 will be specifically described below. The siloxane compound layers in Examples 3 to 5 were formed as in Example 2 except that raw materials used in the preparation of the composition for forming a siloxane compound layer in Example 2 were changed as shown in the table below.

Formation of UV-Curable Silicone Layer

To a 200 mL three-necked flask, 4 g of ES1002T (available from Shin-Etsu Chemical Co., Ltd.) and 96 g of a mixture of n-hexane and n-heptane with a composition ratio of n-hexane:n-heptane=1:3 were added to prepare a silicone polymer solution. Furthermore, 3 g of UV9390C (available from Momentive Performance Materials Inc.) serving as a photopolymerization initiator was added to the silicone polymer solution to prepare a radiation-curable composition. The silicone polymer solution was applied onto a gas separation layer as in Example 1. Subsequently, the resulting membrane was irradiated with UV (Light Hammer 10, D bulb, available from Fusion UV Systems, Inc.) with an illuminance of 1.5 J/cm$^2$. After the irradiation, drying was conducted at 70° C. for two hours to obtain a gas separation membrane (Example 2).

[Examples 6 and 7] Preparation of Asymmetric Flat-Shaped Gas Separation Membranes Gas separation membranes (Examples 6 and 7) were obtained as in Example 1 except that, in Example 1, the raw materials used in the preparation of the composition for forming a siloxane compound layer were changed as shown in a table below, and curing (crosslinking formation) of the siloxane compound layer was conducted by a ligand exchange reaction in the presence of a metal complex shown in the table below.

[Example 8] Preparation of Asymmetric Flat-Shaped Gas Separation Membrane

A gas separation membrane (Example 8) was prepared as in Example 1 except that a siloxane compound layer was not formed on the gas separation layer.

[Example 9] Preparation of Asymmetric Hollow Fiber-Shaped Gas Separation Membrane Preparation of Hollow Fiber The polyimide PI-02 (13.2 g), NMP (23.5 g), 1,3-dioxolane (52.1 g), acetone (4.09 g), and isopropanol (3.04 g) were mixed, and the resulting mixture was degassed to prepare a dope solution. The dope solution was ejected from an outer tube of a cylindrical double tube spinning nozzle (inner tube diameter 0.35 mm, outer tube diameter 1.0 mm) at 50° C. at a flow velocity of 2.25 mL/min, and pure water was simultaneously ejected from an inner tube at a flow velocity of 1.25 mL/min. The ejected dope solution was exposed to air at room temperature and a humidity of 25% for two seconds and then immersed in pure water at 20° C. to prepare a hollow fiber. Subsequently, the hollow fiber was annealed in a water bath at 70° C. for 30 minutes, and the hollow fiber after annealing was washed with water once and with methanol once. Subsequently, the hollow fiber after washing was dried by air blow at 100° C. for five hours and then heat-treated at 400° C. for one hour to form a hollow-fiber membrane having an asymmetric structure and having a gas separation layer formed of PBO-PI-02 shown below. The hollow-fiber membrane had a dense layer with a thickness of 120 nm and a porous layer with a thickness of 70 μm.

Regarding hollow-fiber membranes produced in Examples described below, the thickness of the dense layer and the thickness of the porous layer were respectively controlled to be substantially the same as those of the gas separation membrane of Example 9 (specifically, the difference between the thickness of the dense layer of each of the hollow-fiber membranes and the thickness of the dense layer of Example 9 was controlled within the range of ±20 nm, and the difference between the thickness of the porous layer of each of the hollow-fiber membranes and the thickness of the porous layer of Example 9 was controlled within the range of ±20 μm).

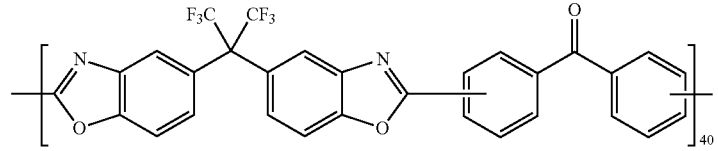

PBO-PI-02

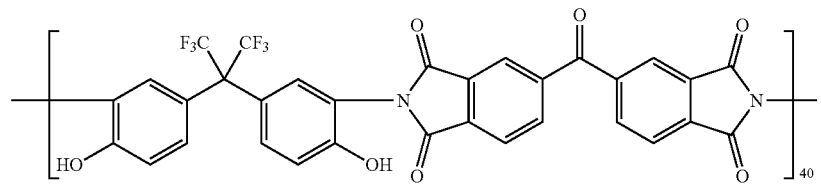

-continued

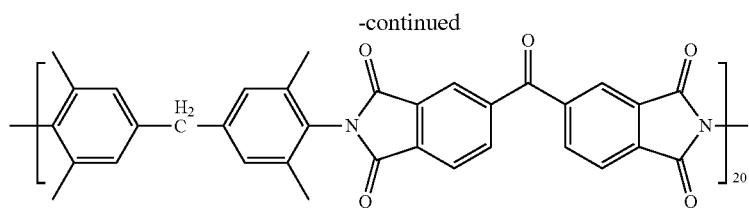

Crosslinking Treatment of Gas Separation Layer

Furthermore, the outer surface of the hollow fiber was irradiated with UV light with an illuminance of 1.5 J/cm² to cure the hollow-fiber membrane.

Formation of Protective Layer

Subsequently, the composition for forming a siloxane compound layer used in Example 1 was applied to the outer surface of the hollow fiber by dip coating and cured by drying at 80° C. for five hours, thus obtaining a gas separation membrane (Example 9) having a siloxane compound layer with a thickness of 700 nm on the gas separation layer. Hereinafter, a gas separation membrane obtained by using a hollow-fiber membrane having an asymmetric structure may be referred to as "asymmetric hollow fiber-shaped gas separation membrane".

[Examples 10 to 17] Preparation of Asymmetric Hollow Fiber-Shaped Gas Separation Membranes Asymmetric hollow fiber-shaped gas separation membranes of Examples 10 to 17 were obtained as in Example 9 except that the types and amounts of the raw materials used in the preparation of the composition for forming a siloxane compound layer were changed as shown in tables below. The ratios of hydrosilyl PDMS to vinyl Q resin in the compositions for forming siloxane compound layers in Examples 10, 11, and 12 are 1/20, 1/40, and 0, respectively, in terms of molar quantity.

[Examples 18 to 29] Preparation of Asymmetric Flat-Shaped Gas Separation Membranes Asymmetric flat-shaped gas separation membranes of Examples 18 to 29 were obtained as in Example 1 except that, in the preparation of the gas separation membrane of Example 1, the polyimides PI-02 to PI-13 were used instead of the polyimide PI-01. The polyimides PI-02 to PI-13 were respectively converted to PBO-PI-02 to PBO-PI-13 by heat treatment (the heat treatment of PI-02, PI-03, and PI-06 to PI-13 was conducted at 400° C. for one hour, the heat treatment of PI-04 was conducted at 350° C. for 2.5 hours, and the heat treatment of PI-05 was conducted at 450° C. for 1.5 hours).

PBO-PI-02

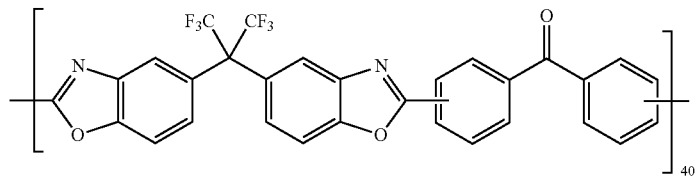

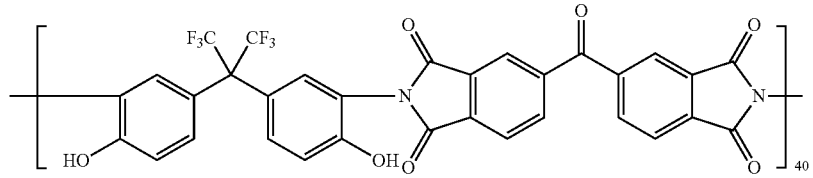

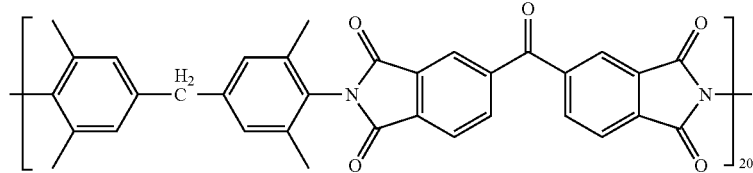

PBO-PI-03

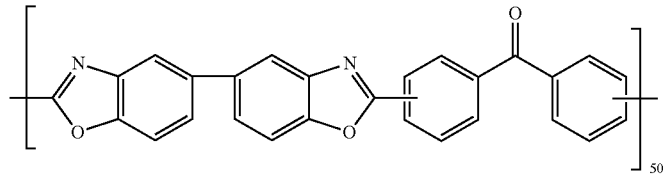

-continued
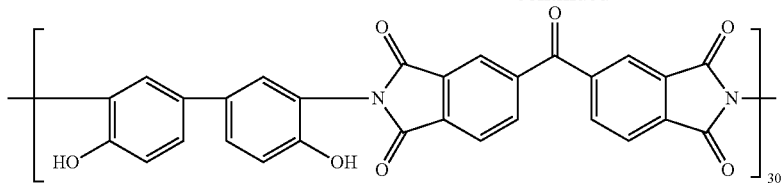
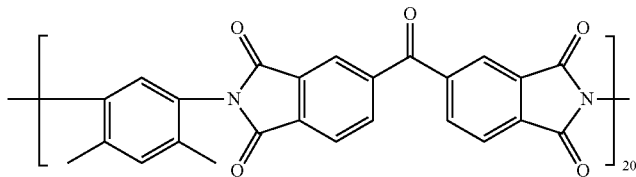
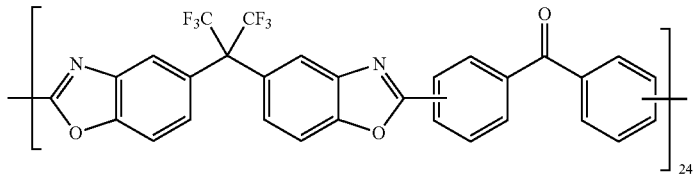
PBO-PI-04
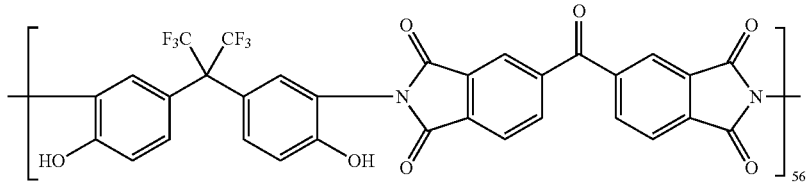
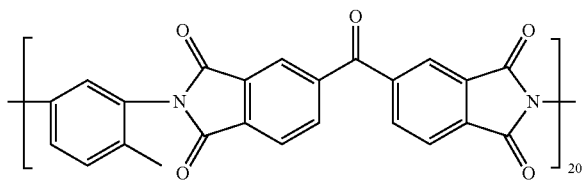
PBO-PI-05
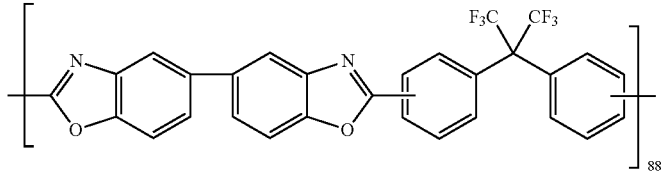
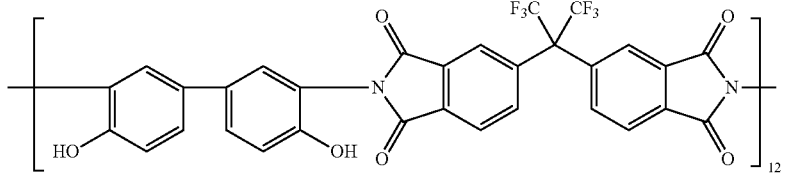
PBO-PI-06
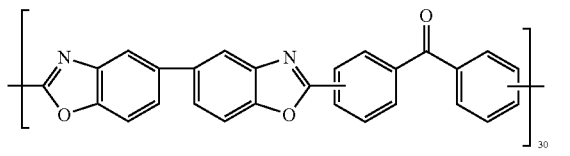 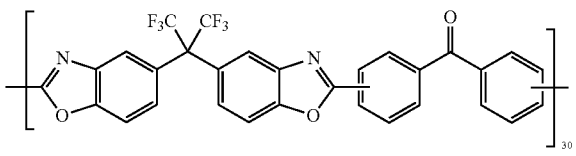
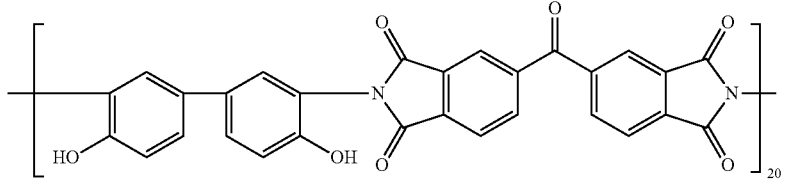

-continued
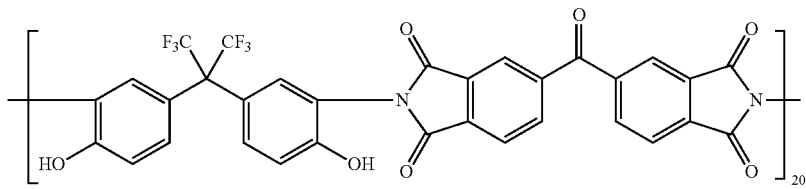
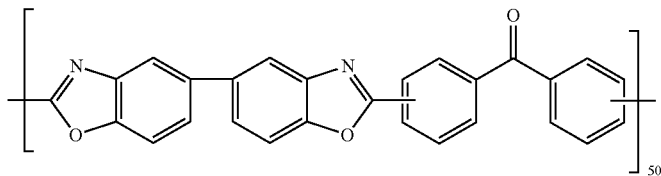
PBO-PI-07
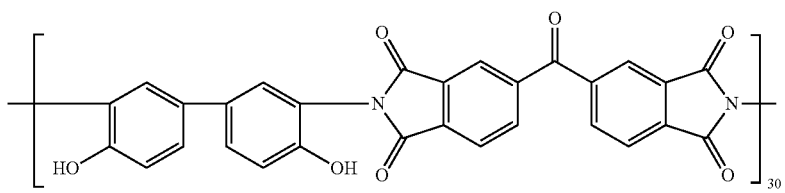
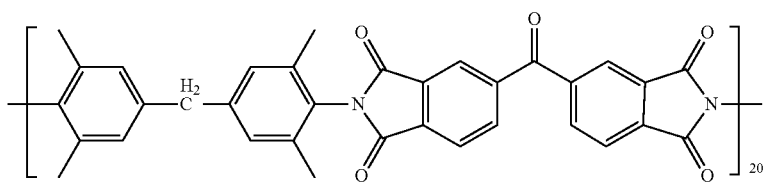
PBO-PI-08
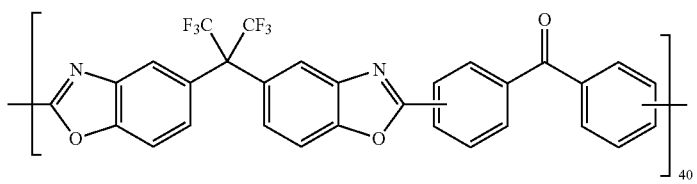
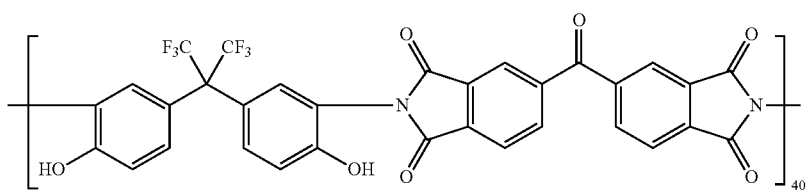
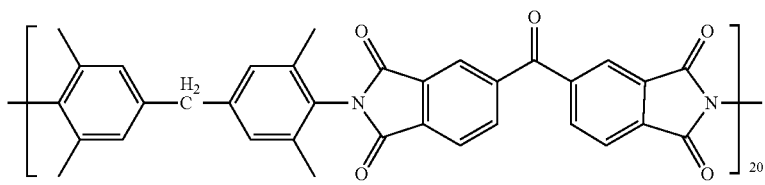
PBO-PI-09
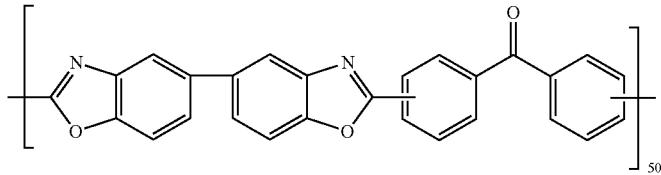

-continued
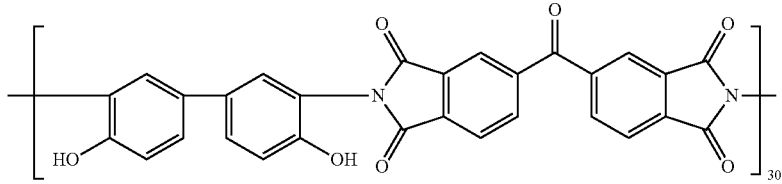
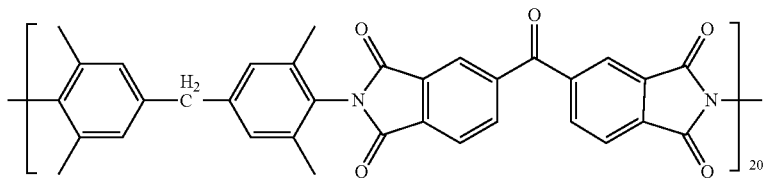
PBO-PI-10
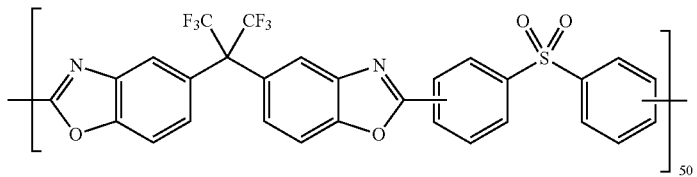
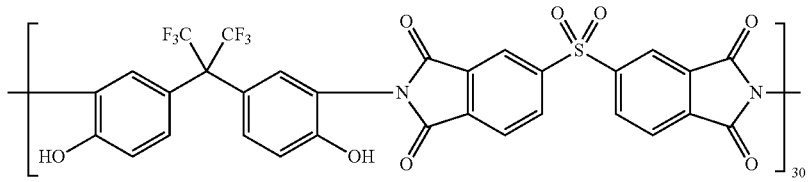
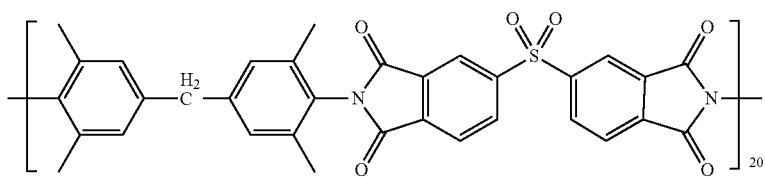
PBO-PI-11
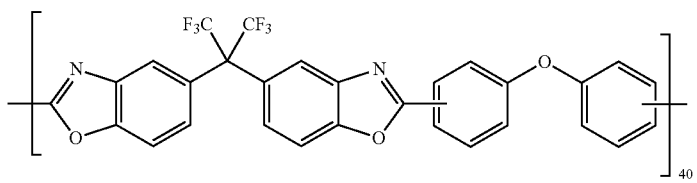
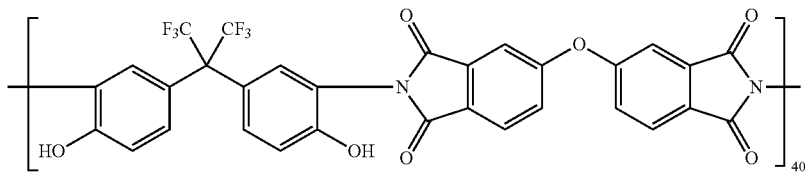
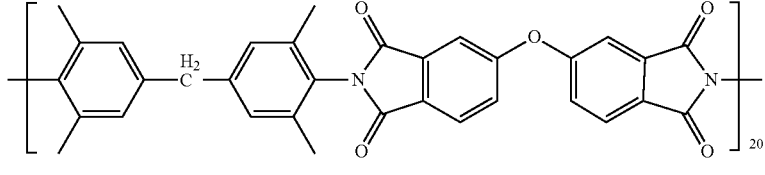
PBO-PI-12
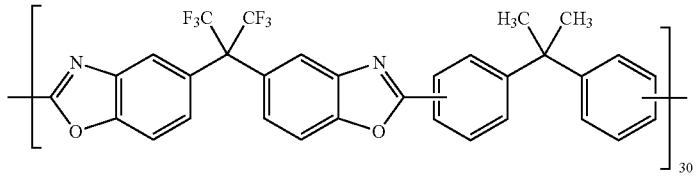

-continued

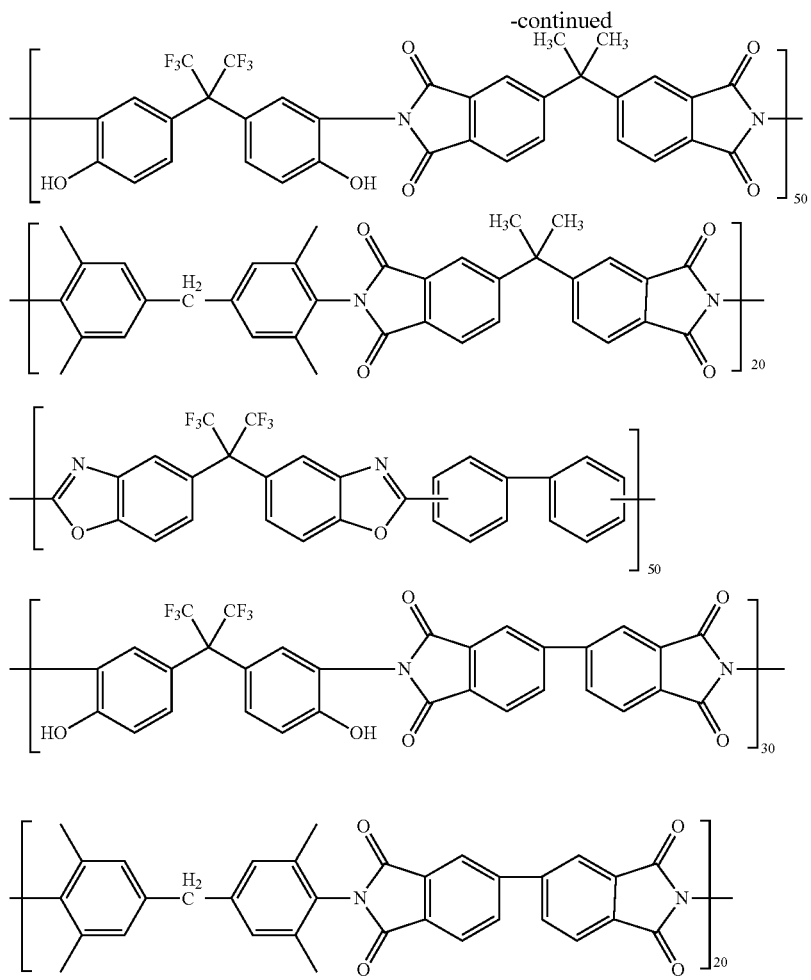

PBO-PI-13

[Examples 30 to 32] Preparation of Asymmetric Flat-Shaped Gas Separation Membranes An asymmetric flat-shaped gas separation membrane of Example 30 was obtained as in Example 1 except that, in the preparation of the gas separation membrane of Example 1, a mixture of the polyimide PI-01 (10.0 g) and polyethersulfone (PES) (3.2 g) was used instead of the polyimide PI-01 (13.2 g).

An asymmetric flat-shaped gas separation membrane of Example 31 was obtained as in Example 1 except that, in the preparation of the gas separation membrane of Example 1, a mixture of the polyimide PI-01 (10.0 g) and polystyrene sulfonate (PSS) (3.2 g) was used instead of the polyimide PI-01 (13.2 g).

An asymmetric flat-shaped gas separation membrane of Example 32 was obtained as in Example 1 except that, in the preparation of the gas separation membrane of Example 1, UV irradiation was not conducted (that is, the curing treatment of the poly(benzoxazole-imide) compound (the crosslinking treatment of the gas separation layer) was not conducted) before the formation of the siloxane compound layer.

Examples 33 and 34

An asymmetric flat-shaped gas separation membrane of Example 33 was obtained as in Example 1 except that, in Example 1, the raw materials used in the preparation of the composition for forming a siloxane compound layer were changed as shown in a table below.

An asymmetric hollow fiber-shaped gas separation membrane of Example 34 was obtained as in Example 9 except that, in Example 9, the raw materials used in the preparation of the composition for forming a siloxane compound layer were changed as shown in the table below.

Comparative Example 1

A flat membrane having an asymmetric structure was prepared as in the preparation of the flat membrane of Example 1 except that, in the preparation of the flat membrane of Example 1, the polyimide PI-05 was used instead of the polyimide PI-01 and heat treatment at 470° C. for two hours was conducted instead of the heat treatment at 400° C. for one hour. The crosslinking treatment of the gas separation layer and the formation of the protective layer were conducted as in Example 1 to obtain a gas separation membrane (Comparative Example 1). In Comparative Example 1, the polyimide PI-05 was converted to PBO-PI-05-02 shown below by the heat treatment at 470° C. for two hours.

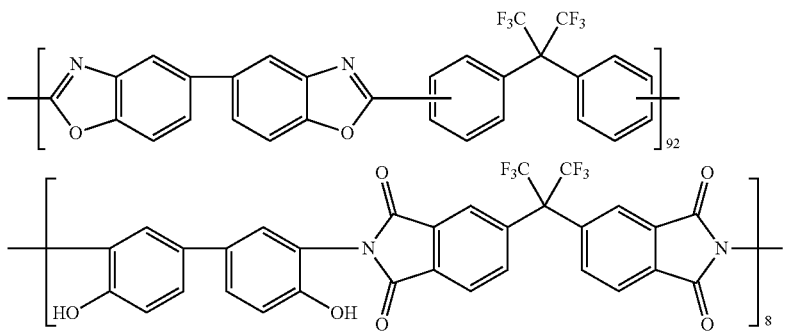

PBO-PI-05-02

Comparative Example 2

An asymmetric flat-shaped gas separation membrane (Comparative Example 2) was obtained as in Comparative Example 1 except that, in Comparative Example 1, heat treatment at 350° C. for 1.5 hours was conducted instead of the heat treatment at 470° C. for two hours. In Comparative Example 2, the polyimide PI-05 was converted to PBO-PI-05-03 shown below by the heat treatment at 350° C. for 1.5 hours.

Tables 1-1 to 1-4 below show structures and physical properties of the gas separation layer and the siloxane compound layer of the gas separation membrane obtained in each of Examples and Comparative Examples.

[Test Example 1] Measurement of Si Ratio of Siloxane Compound Layer

Each of the gas separation membranes (flat membranes) having the siloxane compound layer and prepared in Examples and Comparative Examples was cut out to have a size of 2.5 cm square. The gas separation membrane was immersed in 500 g of chloroform at 25° C. for 12 hours. Subsequently, the gas separation membrane was removed and dried under vacuum. A surface of the gas separation membrane was then irradiated with X-rays (X-ray fluorescence spectrometry, apparatus: XRF-1700 available from Shimadzu Corporation) to measure the intensity of a peak ($2\theta=144.6$ degrees) of the Si–Kα ray of the X-ray fluorescence. The measured value and a value of the Si–Kα X-ray measured by similarly irradiating the surface of the membrane before the immersion in chloroform with X-rays were substituted for Mathematical expression (1) described above to calculate the Si ratio.

Regarding the hollow-fiber membranes, the tube was cut and extended on a flat surface and then applied onto an aluminum plate having a size of 3 cm square without gaps. The Si ratio of this sample was measured by the same method as that used for the flat membranes.

[Test Example 2] Measurement of Content Ratio of Repeating Unit Represented by Formula (5)

Each of the gas separation membranes (flat membranes) prepared in Examples and Comparative Examples was cut

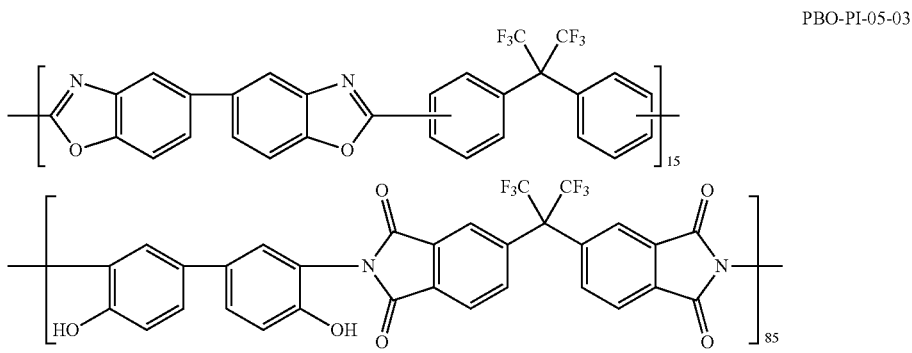

PBO-PI-05-03 out to have a size of 2.5 cm square, thus preparing samples for measurement. The samples for measurement were each subjected to X-ray photoelectron spectroscopy (apparatus: Quantera SXM available from ULVAC-PHI, Incorporated) under conditions of an X-ray source of Al–Kα ray (1490 eV, 25 W, 100 μmφ), a measurement region of 300 μm×300 μM, a pass energy of 55 eV, and a step of 0.05 eV to measure the Si2p (around 98 to 104 eV). Peaks of a T component (103 eV) and a Q component (104 eV) were separated, quantified, and compared. Specifically, a ratio [SA]/([SA]+[ST]) was calculated on the basis of an X-ray fluorescence intensity [SA] of a Si—O bond energy peak of the repeating unit (Q component) represented by Formula (5) and a total intensity [ST] of Si—O bond energy peaks of structures (T component) other than the repeating unit represented by Formula (5). This ratio was defined as the content ratio of the repeating unit represented by Formula (5).

Regarding the hollow-fiber membranes, the tube was cut and extended on a flat surface and then applied onto an aluminum plate having a size of 2.5 cm square without gaps so that the siloxane compound layer was disposed on the upper surface side. The content ratio of the repeating unit represented by Formula (5) was measured by the same method as that used for the flat membranes.

[Test Example 3] Evaluation of Membrane Formability

In accordance with the method described in each of Examples and Comparative Examples, 50 asymmetric gas separation membrane samples were prepared. The permeance of hydrogen of each of the 50 samples was measured. Samples having a hydrogen permeance of more than $1\times10^6$ mL/m$^2$·24 h·atm were determined as membranes having pinholes (sample errors), and a sample error rate was determined by using a formula given below. The membrane formability was evaluated on the basis of the sample error rate in accordance with evaluation criteria, which are described below.

Sample error rate (%)=100×[the number of sample errors/50]

Evaluation Criteria for Membrane Formability
AA: Error rate was 1% or less (that is, no error occurred).
A: Error rate was more than 1% and 3% or less (that is, the number of errors was 1).
B: Error rate was more than 3% and 5% or less (that is, the number of errors was 2).
C: Error rate was more than 5% (that is, the number of errors was 3 or more).
The acceptable level is in the range of AA to B.

[Test Example 4-1] Evaluation of Gas Separation Performance (Evaluation of Flat Membrane)

The gas separation performance was evaluated as described below by using each of the asymmetric flat-shaped gas separation membranes prepared in Examples and Comparative Examples.

The gas separation membranes with nonwoven fabrics were each cut in a circular shape having a diameter of 47 mm to prepare permeation test samples. Mixed gas of carbon dioxide ($CO_2$) and methane ($CH_4$) ($CO_2$:$CH_4$=30:70 (volume ratio)) was adjusted so as to have a total pressure on the gas supply side of 4 MPa (partial pressure of $CO_2$:1.2 MPa), a flow rate of 500 mL/min, and a temperature of 45° C. and supplied from the skin layer side by using a gas permeation analysis system available from GTR Tec Corporation. Gas that had permeated through each of the gas separation membranes was analyzed by gas chromatography. The gas permeabilities of the gas separation membranes were compared to each other by calculating a gas permeation rate as gas permeance. The gas permeance (gas permeation rate) was represented in units of GPU [1 GPU=$1\times10^{-6}$ cm$^3$ (STP)/cm$^2$·sec·cmHg]. The gas separation selectivity was calculated as a ratio ($R_{CO2}/R_{CH4}$) of the permeation rate $R_{CO2}$ of $CO_2$ to the permeation rate $R_{CH4}$ of $CH_4$ of the gas separation membrane.

[Test Example 4-2] Evaluation of Gas Separation Performance (Evaluation of Hollow-Fiber Membrane)

An element for evaluating gas permeation performance, the element having an effective length of 8 cm, was prepared by using six asymmetric hollow-fiber membranes, a stainless pipe, and an epoxy resin-based adhesive. The element was attached to a stainless case to obtain a pencil module. The gas separation performance was evaluated under the same conditions as those of the gas separation performance of the asymmetric flat-shaped gas separation membranes except that gas was supplied to the outside of the hollow-fiber membranes in the module.

[Test Example 5] Evaluation of Folding Endurance

For the asymmetric gas separation membranes prepared by the methods described in Examples and Comparative Examples, an operation of folding and unfolding to the original state was performed 50 times. The gas permeance was then measured as in Test Examples 4-1 and 4-2. The folding endurance was evaluated on the basis of a change in the gas separation selectivity in accordance with evaluation criteria, which are described below.

Folding Conditions
Flat membrane: A planar flat membrane was folded until the radius of curvature became 10 cm. Hollow-fiber membrane: A linear hollow-fiber membrane was folded until the radius of curvature became 10 cm.

Evaluation Criteria for Folding Endurance
AA: Rate of decrease in gas separation selectivity ($R_{CO2}/R_{CH4}$) of an asymmetric gas separation membrane having been subjected to the folding operation relative to gas separation selectivity of an asymmetric gas separation membrane not having been subjected to the folding operation was less than 1%.
A: Rate of decrease in gas separation selectivity ($R_{CO2}/R_{CH4}$) of an asymmetric gas separation membrane having been subjected to the folding operation relative to gas separation selectivity of an asymmetric gas separation membrane not having been subjected to the folding operation was 1% or more and less than 5%.
B: Rate of decrease in gas separation selectivity ($R_{CO2}/R_{CH4}$) of an asymmetric gas separation membrane having been subjected to the folding operation relative to gas separation selectivity of an asymmetric gas separation membrane not having been subjected to the folding operation was 5% or more and less than 20%.
C: Rate of decrease in gas separation selectivity ($R_{CO2}/R_{CH4}$) of an asymmetric gas separation membrane having been subjected to the folding operation relative to gas separation selectivity of an asymmetric gas separation membrane not having been subjected to the folding operation was 20% or more.

The rate of decrease in gas separation selectivity was calculated by the following formula.

Rate of decrease (%)=100−{100×[(gas separation selectivity of asymmetric gas separation membrane having been subjected to folding operation)/(gas separation selectivity of asymmetric gas separation membrane not having been subjected to folding operation)]

The acceptable level is in the range of AA to B.

[Test Example 6] Wet Heat Aging Test

The asymmetric gas separation membranes prepared by the methods described in Examples and Comparative Examples were stored under conditions of 50° C. and a relative humidity of 70% (low-temperature constant temperature and humidity chamber, available from Isuzu Seisakusho Co., Ltd., quartz crystal) for 24 hours. The gas separation selectivity was then determined as in Test Example 4.

[Test Example 7] Toluene Exposure Test

An empty beaker was allowed to stand in a glass container which contained a toluene solvent and to which it was possible to attach a lid to cover the toluene solvent. The asymmetric gas separation membranes prepared in Examples and Comparative Examples were placed in the beaker, and the glass container was sealed by being covered with the glass lid. Subsequently, the asymmetric gas separation membranes were stored at 30° C. for two hours. The gas separation selectivity was then determined as in Test Example 6 by using the asymmetric membranes. This toluene exposure test enables the evaluation of resistance to plasticization of gas separation membranes due to impurity components, such as benzene, toluene, and xylene, which can be present in natural gas.

The results of Test Examples described above are shown in tables below.

Terms described in the tables below mean the following.
"VQM-135": vinyl Q resin (available from Gelest, Inc.)
"ES1002T": epoxy Q resin (available from Shin-Etsu Chemical Co., Ltd.)
"UV-9315": epoxy-modified polydimethylsiloxane (available from Momentive Performance Materials Inc.)
"X-22-164E": methacrylate-modified polydimethylsiloxane (available from Shin-Etsu Chemical Co., Ltd.)
"DMS-S31": hydroxy-modified polydimethylsiloxane (available from Gelest, Inc.)
"DMS-Z21": acid anhydride-modified polydimethylsiloxane (available from Gelest, Inc.)
"X-22-162C": carboxy-modified polydimethylsiloxane (available from Shin-Etsu Chemical Co., Ltd.)
"HMS-301": hydrosilyl-modified polydimethylsiloxane (available from Gelest, Inc.)
"X-22-167B": thiol-modified polydimethylsiloxane (available from Shin-Etsu Chemical Co., Ltd.)
"AMS-162": amine-modified polydimethylsiloxane (available from Gelest, Inc.)
"Photoacid generator": UV9390C available from Momentive Performance Materials Inc.
"Photoradical generator": H0991 available from Tokyo Chemical Industry Co., Ltd. (TCI)
"Karstedt catalyst": 479527 available from Sigma-Aldrich Japan K.K.
"OiPr": isopropoxide
"acac": acetylacetonato
"PBO-PI": poly(benzoxazole-imide) compound
"PES": polyethersulfone
"PSS": polystyrene sulfonate

TABLE 1-1

| | Membrane form | PBO-PI in gas separation layer Type | PBO-PI in gas separation layer m/(n + q) | Polymer other than PBO-PI in gas separation layer Type | Polymer other than PBO-PI in gas separation layer Ratio in all polymers (mass %) | Crosslinking treatment of gas separation layer Treatment condition | Siloxane compound layer Siloxane compound 1 [mass ratio] |
|---|---|---|---|---|---|---|---|
| Example 1 | Flat membrane | PBO-PI-01 | 1.00 | — | — | UV 1.5 J/cm² | VQM-135 [100] |
| Example 2 | Flat membrane | PBO-PI-01 | 1.00 | — | — | UV 1.5 J/cm² | ES1002T [100] |
| Example 3 | Flat membrane | PBO-PI-01 | 1.00 | — | — | UV 1.5 J/cm² | UV-9315 [100] |
| Example 4 | Flat membrane | PBO-PI-01 | 1.00 | — | — | UV 1.5 J/cm² | X-22-164E [100] |
| Example 5 | Flat membrane | PBO-PI-01 | 1.00 | — | — | UV 1.5 J/cm² | ES1002T [100] |
| Example 6 | Flat membrane | PBO-PI-01 | 1.00 | — | — | UV 1.5 J/cm² | DMS-S31 [100] |
| Example 7 | Flat membrane | PBO-PI-01 | 1.00 | — | — | UV 1.5 J/cm² | DMS-S31 [100] |
| Example 8 | Flat membrane | PBO-PI-01 | 1.00 | — | — | UV 1.5 J/cm² | — |
| Example 9 | Hollow fiber | PBO-PI-02 | 0.67 | — | — | UV 1.5 J/cm² | VQM-135 [100] |
| Example 10 | Hollow fiber | PBO-PI-02 | 0.67 | — | — | UV 1.5 J/cm² | VQM-135 [100] |

| | Siloxane compound layer Siloxane compound 2 [mass ratio] | Additive [mass ratio] | Curing treatment | Linking structure between siloxane compounds | Si ratio | Content ratio of repeating unit of Formula (5) |
|---|---|---|---|---|---|---|
| Example 1 | HMS-301 [10] | Karstedt catalyst [0.05] | 80° C. 5 h | —CH₂CH₂— | 0.94 | 0.12 |
| Example 2 | — | Photoacid generator [1] | UV 1.5 J/cm² | —CH₂CH(OH)— | 0.97 | 0.12 |
| Example 3 | — | Photoacid generator [1] | UV 1.5 J/cm² | —CH₂CH(OH)— | 0.98 | 0 |

TABLE 1-1-continued

| | | | | | | |
|---|---|---|---|---|---|---|
| Example 4 | X-22-167B [50] | Photoradical generator [1] | UV 1.5 J/cm² | —CH₂CH₂— —S—CH₂CH₂— | 0.95 | 0 |
| Example 5 | AMS-162 [10] | Photoacid generator [1] | UV 1.5 J/cm² | —CH₂CH(OH)—NH— | 0.92 | 0.15 |
| Example 6 | — | Ti(OiPr)₄ [1] | 80° C. 5 h | —O—Ti—O— | 0.93 | 0 |
| Example 7 | — | Al(acac)₃ [1] | 80° C. 5 h | —O—Al—O— | 0.93 | 0 |
| Example 8 | — | — | — | — | 0 | 0 |
| Example 9 | HMS-301 [10] | Karstedt catalyst [0.05] | 80° C. 5 h | —CH₂CH₂— | 0.94 | 0.12 |
| Example 10 | HMS-301 [5] | Karstedt catalyst [0.05] | 80° C. 5 h | —CH₂CH₂— | 0.94 | 0.13 |

TABLE 1-2

| | Membrane form | PBO-PI in gas separation layer Type | PBO-PI in gas separation layer m/(n + q) | Polymer other than PBO-PI in gas separation layer Type | Polymer other than PBO-PI in gas separation layer Ratio in all polymers (mass %) | Crosslinking treatment of gas separation layer Treatment condition | Siloxane compound layer Siloxane compound 1 [mass ratio] |
|---|---|---|---|---|---|---|---|
| Example 11 | Hollow fiber | PBO-PI-02 | 0.67 | — | — | UV 1.5 J/cm² | VQM-135 [100] |
| Example 12 | Hollow fiber | PBO-PI-02 | 0.67 | — | — | UV 1.5 J/cm² | VQM-135 [100] |
| Example 13 | Hollow fiber | PBO-PI-02 | 0.67 | — | — | UV 1.5 J/cm² | DMS-Z21 [100] |
| Example 14 | Hollow fiber | PBO-PI-02 | 0.67 | — | — | UV 1.5 J/cm² | X-22-162C [100] |
| Example 15 | Hollow fiber | PBO-PI-02 | 0.67 | — | — | UV 1.5 J/cm² | Teflon 60 |
| Example 16 | Hollow fiber | PBO-PI-02 | 0.67 | — | — | UV 1.5 J/cm² | Non-functional PDMS |
| Example 17 | Hollow fiber | PBO-PI-02 | 0.67 | — | — | UV 1.5 J/cm² | — |
| Example 18 | Flat membrane | PBO-PI-02 | 0.67 | — | — | UV 1.5 J/cm² | VQM-135 [100] |

| | Siloxane compound layer Siloxane compound 2 [mass ratio] | Additive [mass ratio] | Curing treatment | Linking structure between siloxane compounds | Si ratio | Content ratio of repeating unit of Formula (5) |
|---|---|---|---|---|---|---|
| Example 11 | HMS-301 [2.5] | Karstedt catalyst [0.05] | 80° C. 5 h | —CH₂CH₂— | 0.36 | 0.13 |
| Example 12 | — | Karstedt catalyst [0.05] | 80° C. 5 h | —CH₂CH₂— | 0 | 0 |
| Example 13 | AMS-162 [150] | DBU [5] | 100° C. 5 h | Imide bond | 0.92 | 0 |
| Example 14 | — | In(acas)₃ [1] | 100° C. 5 h | —O—In—O— | 0.86 | 0 |
| Example 15 | — | — | 80° C. 5 h | — | 0 | 0 |
| Example 16 | — | — | 80° C. 5 h | — | 0 | 0 |
| Example 17 | — | — | — | — | 0 | 0 |
| Example 18 | HMS-301 [10] | Karstedt catalyst [0.05] | 80° C. 5 h | —CH₂CH₂— | 0.94 | 0.12 |

TABLE 1-3

| | Membrane form | PBO-PI in gas separation layer Type | PBO-PI in gas separation layer m/(n + q) | Polymer other than PBO-PI in gas separation layer Type | Polymer other than PBO-PI in gas separation layer Ratio in all polymers (mass %) | Crosslinking treatment of gas separation layer Treatment condition | Siloxane compound layer Siloxane compound 1 [mass ratio] |
|---|---|---|---|---|---|---|---|
| Example 19 | Flat membrane | PBO-PI-03 | 1.00 | — | — | UV 1.5 J/cm² | VQM-135 [100] |
| Example 20 | Flat membrane | PBO-PI-04 | 0.32 | — | — | UV 1.5 J/cm² | VQM-135 [100] |
| Example 21 | Flat membrane | PBO-PI-05 | 7.33 | — | — | UV 1.5 J/cm² | VQM-135 [100] |
| Example 22 | Flat membrane | PBO-PI-06 | 1.50 | — | — | UV 1.5 J/cm² | VQM-135 [100] |
| Example 23 | Flat membrane | PBO-PI-07 | 1.00 | — | — | UV 1.5 J/cm² | VQM-135 [100] |
| Example 24 | Flat membrane | PBO-PI-08 | 0.67 | — | — | UV 1.5 J/cm² | VQM-135 [100] |
| Example 25 | Flat membrane | PBO-PI-09 | 1.00 | — | — | UV 1.5 J/cm² | VQM-135 [100] |
| Example 26 | Flat membrane | PBO-PI-10 | 1.00 | — | — | UV 1.5 J/cm² | VQM-135 [100] |
| Example 27 | Flat membrane | PBO-PI-11 | 0.67 | — | — | UV 1.5 J/cm² | VQM-135 [100] |
| Example 28 | Flat membrane | PBO-PI-12 | 0.43 | — | — | UV 1.5 J/cm² | VQM-135 [100] |

| | Siloxane compound layer Siloxane compound 2 [mass ratio] | Siloxane compound layer Additive [mass ratio] | Siloxane compound layer Curing treatment | Siloxane compound layer Linking structure between siloxane compounds | Siloxane compound layer Si ratio | Siloxane compound layer Content ratio of repeating unit of Formula (5) |
|---|---|---|---|---|---|---|
| Example 19 | HMS-301 [10] | Karstedt cataylst [0.05] | 80° C. 5 h | —CH$_2$CH$_2$— | 0.94 | 0.12 |
| Example 20 | HMS-301 [10] | Karstedt cataylst [0.05] | 80° C. 5 h | —CH$_2$CH$_2$— | 0.94 | 0.12 |
| Example 21 | HMS-301 [10] | Karstedt cataylst [0.05] | 80° C. 5 h | —CH$_2$CH$_2$— | 0.94 | 0.12 |
| Example 22 | HMS-301 [10] | Karstedt cataylst [0.05] | 80° C. 5 h | —CH$_2$CH$_2$— | 0.94 | 0.12 |
| Example 23 | HMS-301 [10] | Karstedt cataylst [0.05] | 80° C. 5 h | —CH$_2$CH$_2$— | 0.94 | 0.12 |
| Example 24 | HMS-301 [10] | Karstedt cataylst [0.05] | 80° C. 5 h | —CH$_2$CH$_2$— | 0.94 | 0.12 |
| Example 25 | HMS-301 [10] | Karstedt cataylst [0.05] | 80° C. 5 h | —CH$_2$CH$_2$— | 0.94 | 0.12 |
| Example 26 | HMS-301 [10] | Karstedt cataylst [0.05] | 80° C. 5 h | —CH$_2$CH$_2$— | 0.94 | 0.12 |
| Example 27 | HMS-301 [10] | Karstedt cataylst [0.05] | 80° C. 5 h | —CH$_2$CH$_2$— | 0.94 | 0.12 |
| Example 28 | HMS-301 [10] | Karstedt cataylst [0.05] | 80° C. 5 h | —CH$_2$CH$_2$— | 0.94 | 0.12 |

TABLE 1-4

| | Membrane form | PBO-PI in gas separation layer Type | PBO-PI in gas separation layer m/(n+q) | Polymer other than PBO-PI in gas separation layer Type | Polymer other than PBO-PI in gas separation layer Ratio in all polymers (mass %) | Crosslinking treatment of gas separation layer Treatment condition | Siloxane compound layer Siloxane compound 1 [mass ratio] |
|---|---|---|---|---|---|---|---|
| Example 29 | Flat membrane | PBO-PI-13 | 1.00 | — | — | UV 1.5 J/cm² | VQM-135 [100] |
| Example 30 | Flat membrane | PBO-PI-01 | 1.00 | PES | 25 | UV 1.5 J/cm² | VQM-135 [100] |
| Example 31 | Flat membrane | PBO-PI-01 | 1.00 | PSS | 25 | UV 1.5 J/cm² | VQM-135 [100] |
| Example 32 | Flat membrane | PBO-PI-01 | 1.00 | — | — | UV 1.5 J/cm² | VQM-135 [100] |
| Example 33 | Flat membrane | PBO-PI-01 | 1.00 | — | — | UV 1.5 J/cm² | VQM-135 [100] |
| Example 34 | Hollow fiber | PBO-PI-02 | 1.00 | — | — | UV 1.5 J/cm² | VQM-135 [100] |
| Com. Ex. 1 | Flat membrane | PBO-PI-05-02 | 11.5 | — | — | UV 1.5 J/cm² | VQM-135 [100] |
| Com. Ex. 2 | Flat membrane | PBO-PI-05-03 | 0.18 | — | — | UV 1.5 J/cm² | VQM-135 [100] |

| | Siloxane compound 2 [mass ratio] | Additive [mass ratio] | Curing treatment | Linking structure between siloxane compounds | Si ratio | Content ratio of repeating unit of Formula (5) |
|---|---|---|---|---|---|---|
| Example 29 | HMS-301 [10] | Karstedt cataylst [0.05] | 80° C. 5 h | —CH₂CH₂— | 94 | 0.12 |
| Example 30 | HMS-301 [10] | Karstedt cataylst [0.05] | 80° C. 5 h | —CH₂CH₂— | 94 | 0.12 |
| Example 31 | HMS-301 [10] | Karstedt cataylst [0.05] | 80° C. 5 h | —CH₂CH₂— | 94 | 0.12 |
| Example 32 | HMS-301 [10] | Karstedt cataylst [0.05] | 80° C. 5 h | —CH₂CH₂— | 94 | 0.12 |
| Example 33 | HMS-301 [10] | Karstedt cataylst [0.05] Al(acac)₃ [1] | 80° C. 5 h | —CH₂CH₂— —O—Al—O— | 94 | 0.12 |
| Example 34 | HMS-301 [10] | Karstedt cataylst [0.05] Al(acac)₃ [1] | 80° C. 5 h | —CH₂CH₂— —O—Al—O— | 94 | 0.12 |
| Com. Ex. 1 | HMS-301 [10] | Karstedt cataylst [0.05] | 80° C. 5 h | —CH₂CH₂— | 94 | 0.12 |
| Com. Ex. 2 | HMS-301 [10] | Karstedt cataylst [0.05] | 80° C. 5 h | —CH₂CH₂— | 94 | 0.12 |

Com. Ex.: Comparative Example

TABLE 2

| | Membrane formability | Folding endurance | $CO_2$ permeance [GPU] | $R_{CO2}/R_{CH4}$ Untreated | $R_{CO2}/R_{CH4}$ After wet heat test | $R_{CO2}/R_{CH4}$ After toluene exposure test |
|---|---|---|---|---|---|---|
| Example 1 | AA | AA | 90 | 44 | 43 | 42 |
| Example 2 | A | AA | 79 | 42 | 40 | 38 |
| Example 3 | A | A | 92 | 41 | 40 | 37 |
| Example 4 | A | A | 91 | 41 | 39 | 36 |

TABLE 2-continued

| | Membrane formability | Folding endurance | CO$_2$ permeance [GPU] | $R_{CO2}/R_{CH4}$ Untreated | After wet heat test | After toluene exposure test |
|---|---|---|---|---|---|---|
| Example 5 | A | AA | 88 | 42 | 40 | 39 |
| Example 6 | A | A | 90 | 39 | 38 | 37 |
| Example 7 | A | A | 85 | 40 | 38 | 36 |
| Example 8 | B | A | 82 | 38 | 31 | 21 |
| Example 9 | AA | AA | 85 | 41 | 39 | 38 |
| Example 10 | A | AA | 85 | 40 | 36 | 34 |
| Example 11 | B | A | 79 | 38 | 35 | 29 |
| Example 12 | B | A | 88 | 34 | 32 | 22 |
| Example 13 | A | A | 79 | 36 | 36 | 32 |
| Example 14 | A | A | 79 | 32 | 32 | 31 |
| Example 15 | A | A | 38 | 35 | 35 | 32 |
| Example 16 | B | A | 43 | 39 | 39 | 29 |
| Example 17 | B | B | 85 | 31 | 31 | 20 |
| Example 18 | AA | AA | 100 | 39 | 39 | 38 |
| Example 19 | A | AA | 89 | 40 | 36 | 35 |
| Example 20 | A | A | 72 | 36 | 33 | 31 |
| Example 21 | B | B | 90 | 32 | 31 | 29 |
| Example 22 | A | A | 89 | 34 | 31 | 30 |
| Example 23 | A | AA | 86 | 42 | 42 | 41 |
| Example 24 | A | AA | 80 | 42 | 42 | 41 |
| Example 25 | A | A | 86 | 40 | 40 | 36 |
| Example 26 | A | A | 90 | 40 | 40 | 37 |
| Example 27 | A | B | 86 | 42 | 42 | 41 |
| Example 28 | B | A | 80 | 30 | 30 | 22 |
| Example 29 | B | A | 72 | 42 | 42 | 41 |
| Example 30 | AA | AA | 90 | 43 | 43 | 42 |
| Example 31 | AA | AA | 85 | 45 | 45 | 43 |
| Example 32 | A | AA | 81 | 38 | 34 | 30 |
| Example 33 | AA | AA | 92 | 48 | 46 | 46 |
| Example 34 | AA | AA | 95 | 47 | 45 | 44 |
| Comparative Example 1 | C | C | 60 | 14 | 14 | 9 |
| Comparative Example 2 | B | B | 40 | 30 | 25 | 22 |

As shown in the results in Table 2, the gas separation membrane of Comparative Example 1 in which the structure of the poly(benzoxazole-imide) compound did not satisfy the relationship 0.25≤m/(n+q)≤9.00 (0<n, 0≤q) had low gas permeability and poor gas separation selectivity. In addition, the gas separation membrane of Comparative Example 1 had significantly poor membrane formability and folding endurance. The results showed that, in contrast, the gas separation membranes of Examples 1 to 34, which satisfied the condition of the present invention, had good gas permeability and gas separation selectivity and had good membrane formability and folding endurance.

These results showed that a good gas separation method, a good gas separation module, and a gas separation apparatus including the gas separation module can be provided by using the gas separation membrane of the present invention.

REFERENCE SIGNS LIST

10, 20, 30, 40: composite gas separation membrane
1: gas separation layer
2: porous layer
3: nonwoven fabric layer
4: siloxane compound layer (protective layer)
5: siloxane compound layer (smooth layer)
50, 60: asymmetric gas separation membrane
C: siloxane compound layer (protective layer)
S: dense layer (skin layer, gas separation layer)
P: porous layer
6: pore

What is claimed is:
1. A gas separation membrane comprising:
a gas separation layer containing a poly(benzoxazole-imide) compound,
wherein the poly(benzoxazole-imide) compound satisfies a condition (A) or (B):
(A) the poly(benzoxazole-imide) compound has a structural unit represented by General formula (I) and a structural unit represented by General formula (II), and
in the poly(benzoxazole-imide) compound, a molar quantity m of the structural unit represented by General formula (I) and a molar quantity n of the structural unit represented by General formula (II) satisfy Mathematical expression 1;
(B) the poly(benzoxazole-imide) compound has the structural unit represented by General formula (I), the structural unit represented by General formula (II), and a structural unit represented by General formula (III), and
in the poly(benzoxazole-imide) compound, the molar quantity m of the structural unit represented by General formula (I), the molar quantity n of the structural unit represented by General formula (II), and a molar quantity q of the structural unit represented by General formula (III) satisfy Mathematical expression 2:

$$0.25 \leq m/n \leq 9.00 (0<n),$$  Mathematical expression 1:

$$0.25 \leq m/(n+q) \leq 9.00 (0<n, 0<q),$$  Mathematical expression 2:

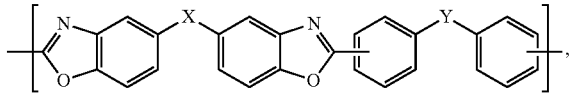

General formula (I)

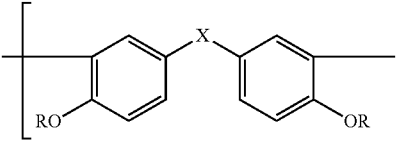

General formula (II)

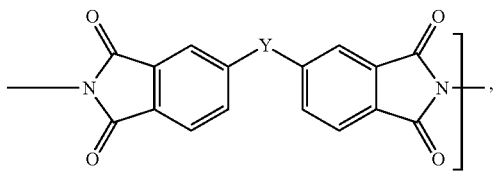

General formula (III)

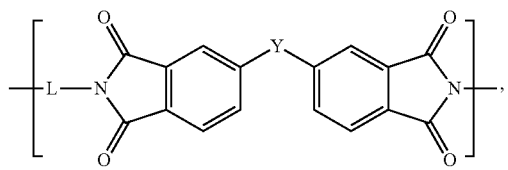

where X and Y each represent a single bond, a divalent linking group selected from Group (IV) of linking groups, or a divalent linking group formed by combining one or two or more linking groups selected from Group (IV);
L represents a divalent linking group including a phenylene group provided that the phenylene group does not have an —OR group as a substituent; and
R represents COR$^1$ or Si(R$^2$)$_3$ where R$^1$ and R$^2$ each represent an alkyl group, Group (IV)

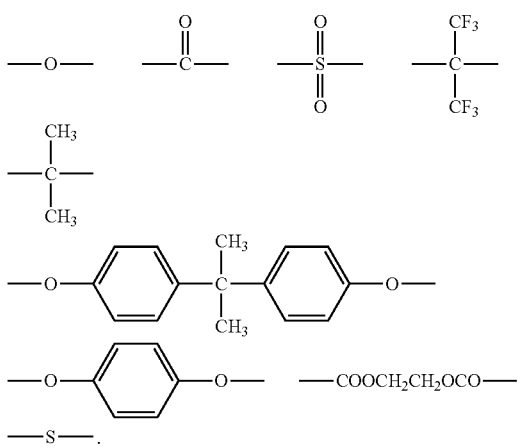

2. The gas separation membrane according to claim 1, wherein the poly(benzoxazole-imide) compound satisfies the condition (B), and L is a divalent linking group selected from Group (V), Group (V)

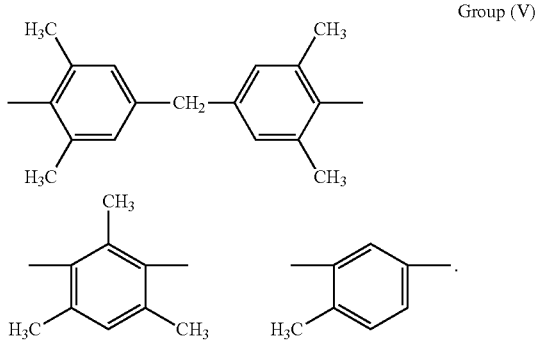

3. The gas separation membrane according to claim 2, wherein L is a divalent linking group represented by the following formula

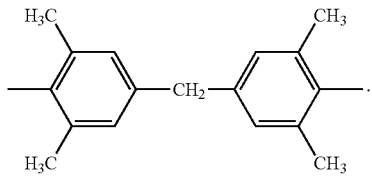

4. The gas separation membrane according to claim 1, wherein Y is a single bond or a divalent linking group selected from Group (IV-1), Group (IV-1)

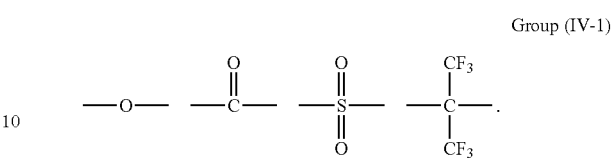

5. The gas separation membrane according to claim 1, wherein Y is a divalent linking group selected from Group (IV-2), Group (IV-2)

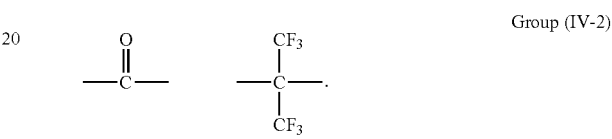

6. The gas separation membrane according to claim 1, wherein Y is a divalent linking group represented by the following formula

7. The gas separation membrane according to claim 1, wherein X is a single bond or a divalent linking group represented by the following formula

8. The gas separation membrane according to claim 1, wherein the gas separation layer further contains a polymer other than the poly(benzoxazole-imide) compound.

9. The gas separation membrane according to claim 1, wherein the gas separation layer is formed by heat-treating a layer containing a polyimide compound having a structural unit represented by General formula (VI) and a structural unit represented by General formula (VII), General formula (VI)

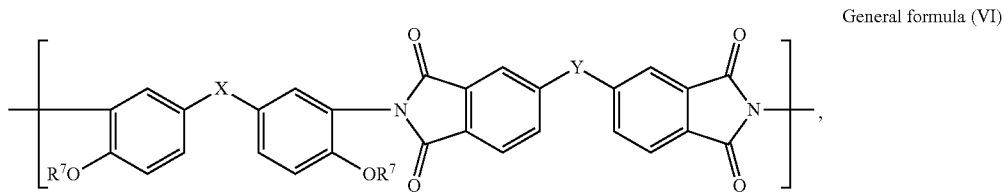

-continued

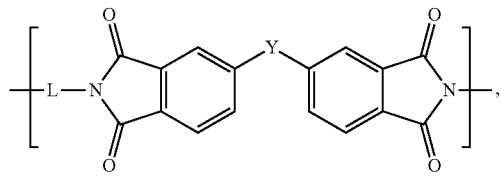

where X, Y, and L respectively have the same definition as X, Y, and L in General formulae (II) and (III); and $R^Z$ represents a $COR^1$ or $Si(R^2)_3$ where $R^1$ and $R^2$ each represent an alkyl group.

10. The gas separation membrane according to claim 9, wherein $R^Z$ is $COR^1$ or $Si(R^2)_3$ where $R^1$ and $R^2$ each represent an alkyl group.

11. The gas separation membrane according to claim 9, wherein $R^Z$ is $COR^1$ where $R^1$ represents an alkyl group.

12. The gas separation membrane according to claim 9, wherein $R^Z$ is $COCH_3$.

13. The gas separation membrane according to claim 9, wherein $R^Z$ is $Si(R^2)_3$ where $R^2$ represents an alkyl group.

14. The gas separation membrane according to claim 9, wherein a temperature of the heat-treating is 300° C. to 600° C.

15. The gas separation membrane according to claim 1, wherein the gas separation membrane is an asymmetric membrane.

16. The gas separation membrane according to claim 1, further comprising:
a siloxane compound layer disposed on the gas separation layer,
wherein a Si ratio of the siloxane compound layer after immersion in chloroform to the siloxane compound layer before immersion in chloroform, the Si ratio being calculated by Mathematical expression (I), is 0.6 to 1.0, Si ratio=(Si-Kα X-ray intensity after immersion in chloroform)/(Si-Kα X-ray intensity before immersion in chloroform),  Mathematical expression (1).

17. The gas separation membrane according to claim 16, wherein the siloxane compound layer contains an organopolysiloxane compound having a structure in which siloxane compounds are linked to each other through a linking group selected from the group consisting of *—O-M-O—*, *—S-M-S—*, *—$NR^aC$(=O)—*, *—$NR^bC$(=O)$NR^b$—*, *—O—$CH_2$—O—*, *—S—$CH_2CH_2$—*, *—OC(=O) O—*, *—CH(OH)$CH_2$OCO—*, *—CH(OH)$CH_2$O—*, *—CH(OH)$CH_2$S—*, *—CH(OH)$CH_2NR^c$—*, *—CH($CH_2$OH)$CH_2$OCO—*, *—CH($CH_2$OH)$CH_2$O—*, *—CH($CH_2$OH)$CH_2$S—*, *—CH($CH_2$OH)$CH_2NR^c$—*, *—$CH_2CH_2$—*, *—C(=O)$O^-N^+(R^e)_3$—*, *—$SO_3^-N^+$($R^e$)$_3$—*, and *—$PO_3H^-N^+(R^f)_3$—*,
where M represents a divalent to tetravalent metal atom; $R^a$, $R^b$, $R^c$, $R^d$, $R^e$, and $R^f$ each independently represent a hydrogen atom or an alkyl group; and the symbol * represents a linking site.

18. The gas separation membrane according to claim 17, wherein the metal atom M is a metal atom selected from the group consisting of Be, Mg, Ca, Sc, Y, Ti, Zr, V, Cr, Mo, Mn, Fe, Co, Ni, Cu, Zn, B, Al, Ga, and In.

19. The gas separation membrane according to claim 16, wherein the siloxane compound layer has at least one structure represented by (a) or (b);

(a) a structure having a structure represented by General formula (1) and a structure represented by General formula (2) or General formula (3), and (b) a structure represented by General formula (4), General formula (1)

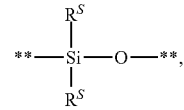

General formula (2)

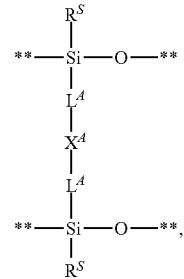

General formula (3)

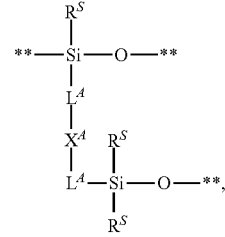

General formula (4)

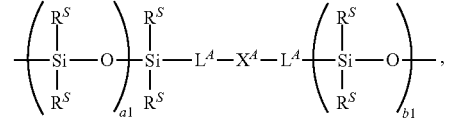

where $R^S$ represents an alkyl group or an aryl group; $L^A$ represents a single bond or a divalent linking group; $X^A$ represents a linking group selected from the group consisting of *—O-$M^1$-O—*, *—S-$M^1$-S—*, *—O—$CH_2$—O—*, *—S—$CH_2CH_2$—*, *—OC(=O)O—*, *—$CH_2CH_2$—*, and *—C(=O)$O^-N^+(R^d)_3$—*, where $M^1$ represents Zr, Fe, Zn, B, Al, Ti, In, or Ga; $R^d$ represents a hydrogen atom or an alkyl group; a1 and b1 are each an integer of 2 or more; the symbol * represents a linking site; and the symbol ** represents a linking site in a siloxane bond.

20. The gas separation membrane according to claim 19, wherein the structure of (a) further has a repeating unit represented by Formula (5), Formula (5)

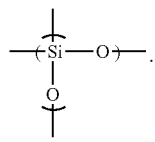

21. The gas separation membrane according to claim 20, wherein a content ratio of the repeating unit represented by Formula (5) in the siloxane compound layer is 0.01 to 0.55.

22. A gas separation module comprising the gas separation membrane according to claim 1.

23. A gas separation apparatus comprising the gas separation module according to claim 22.

24. A gas separation method comprising supplying gas to the gas separation membrane according to claim 1.

25. The gas separation method according to claim 24, wherein carbon dioxide is selectively permeated through the gas separation membrane to be separated from methane contained in the gas.

26. A gas separation membrane comprising:
- a gas separation layer containing a poly(benzoxazole-imide) compound,
- wherein the poly(benzoxazole-imide) compound has a structural unit represented by General formula (I), a structural unit represented by General formula (II), and a structural unit represented by General formula (III), and
- in the poly(benzoxazole-imide) compound, the molar quantity m of the structural unit represented by General formula (I), the molar quantity n of the structural unit represented by General formula (II), and a molar quantity q of the structural unit represented by General formula (III) satisfy the following Mathematical expression:

$0.25 \leq m/(n+q) \leq 9.00 \ (0<n, \ 0<q)$,

General formula (I)
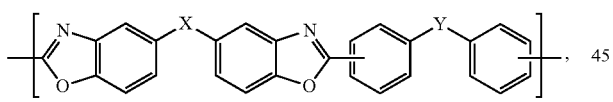

General formula (II)
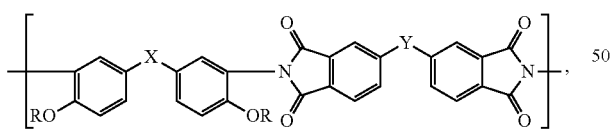

General formula (III)
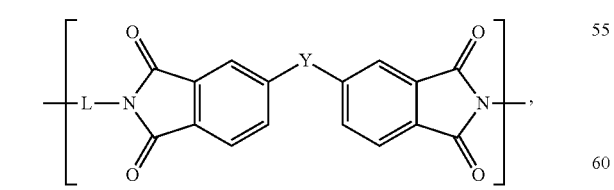

where X and Y each represent a single bond, a divalent linking group selected from Group (IV) of linking groups, or a divalent linking group formed by combining one or two or more linking groups selected from Group (IV);

L represents a divalent linking group selected from Group (V); and

R represents a hydrogen atom, $COR^1$, or $Si(R^2)_3$ where $R^1$ and $R^2$ each represent an alkyl group, Group (IV)
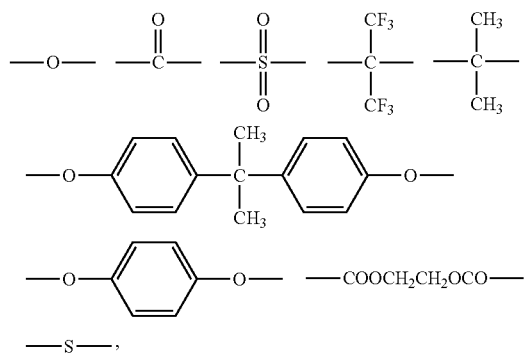

Group (V)
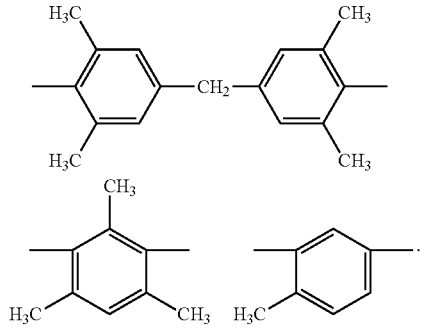

27. A gas separation membrane comprising:
- a gas separation layer containing a poly(benzoxazole-imide) compound,
- wherein the poly(benzoxazole-imide) compound has a structural unit represented by General formula (I), a structural unit represented by General formula (II), and a structural unit represented by General formula (III), and
- in the poly(benzoxazole-imide) compound, the molar quantity m of the structural unit represented by General formula (I), the molar quantity n of the structural unit represented by General formula (II), and a molar quantity q of the structural unit represented by General formula (III) satisfy the following Mathematical expression:

$0.25 \leq m/(n+q) \leq 9.00 \ (0<n, \ 0<q)$,

General formula (I)
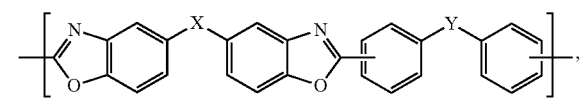

-continued

General formula (II)

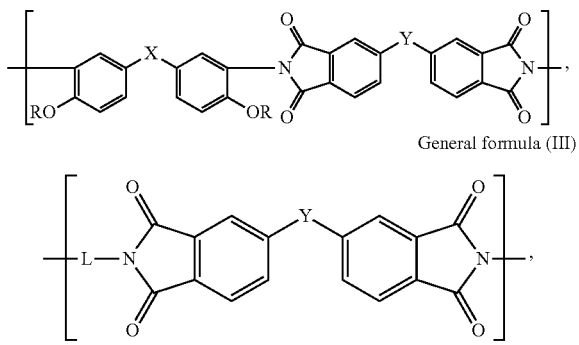

General formula (III)

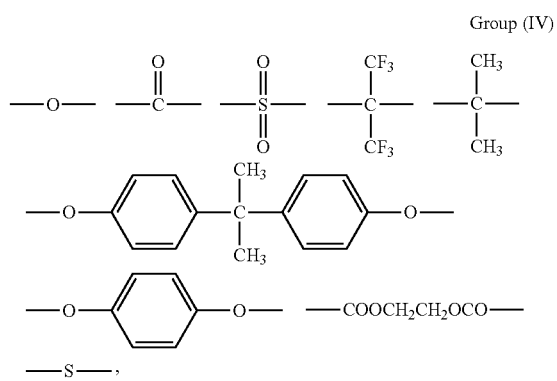

where X and Y each represent a single bond, a divalent linking group selected from Group (IV) of linking groups, or a divalent linking group formed by combining one or two or more linking groups selected from Group (IV);

L represents a divalent linking group including a phenylene group provided that the phenylene group does not have an —OR group as a substituent; and R represents a hydrogen atom, $COR^1$, or $Si(R^2)_3$ where $R^1$ and $R^2$ each represent an alkyl group, Group (IV)

—O—   —C(=O)—   —S(=O)$_2$—   —C(CF$_3$)$_2$—   —C(CH$_3$)$_2$—

—O—C$_6$H$_4$—C(CH$_3$)$_2$—C$_6$H$_4$—O—

—O—C$_6$H$_4$—O—   —COOCH$_2$CH$_2$OCO—

—S—, and the gas separation layer is formed by heat-treating a layer containing a polyimide compound having a structural unit represented by General formula (II) and a structural unit represented by General formula (III).

* * * * *